(12) United States Patent
Ueda et al.

(10) Patent No.: US 12,077,524 B2
(45) Date of Patent: Sep. 3, 2024

(54) CRYSTAL OF PYRROLIDINE COMPOUND

(71) Applicant: MITSUBISHI TANABE PHARMA CORPORATION, Osaka (JP)

(72) Inventors: Naoko Ueda, Osaka (JP); Hiroomi Nagata, Osaka (JP); Takahiro Yoshida, Osaka (JP)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 594 days.

(21) Appl. No.: 17/418,563

(22) PCT Filed: Dec. 27, 2019

(86) PCT No.: PCT/JP2019/051570
§ 371 (c)(1),
(2) Date: Jun. 25, 2021

(87) PCT Pub. No.: WO2020/138481
PCT Pub. Date: Jul. 2, 2020

(65) Prior Publication Data
US 2022/0073497 A1    Mar. 10, 2022

(30) Foreign Application Priority Data
Dec. 28, 2018 (JP) ................. 2018-247437

(51) Int. Cl.
*C07D 401/14* (2006.01)

(52) U.S. Cl.
CPC ........ *C07D 401/14* (2013.01); *C07B 2200/13* (2013.01)

(58) Field of Classification Search
CPC ............. C07D 401/14; C07B 2200/13
USPC ........................................... 514/326
See application file for complete search history.

(56) References Cited

U.S. PATENT DOCUMENTS

| 9,981,960 | B2 * | 5/2018 | Yamamoto | ......... A61K 31/5377 |
| 2008/0057074 | A1 | 3/2008 | Takoaka et al. | |
| 2017/0190697 | A1 * | 7/2017 | Yamamoto | ........... C07D 403/04 |

FOREIGN PATENT DOCUMENTS

| JP | 2017-105765 A | 6/2017 |
| WO | WO 2015/182723 A1 | 12/2015 |

OTHER PUBLICATIONS

CDC, Picture of America Prevention, pp. 1-9, https://www.cdc.gov/pictureofamerica/pdfs/picture_of_america_prevention.pdf, accessed Dec. 8, 2023, first published Jul. 2, 2017 (Year: 2017).*
CDC, Picture of America Prevention, p. 1, https://www.cdc.gov/pictureofamerica/pdfs/picture_of_america_prevention.pdf, accessed Dec. 8, 2023, first published Jul. 2, 2017, Wayback Machine (Year: 2017).*
Ericson et al., Published Oct. 2017, BBA—Molecular Basis of Disease, vol. 1863, Issue 10, Part A, pp. 2414-2435 (Year: 2017).*
Wolf Horrell et al., Published May 2016, frontiers in Genetics, vol. 7, pp. 1-16 (Year: 2016).*
Loram et al., Published Feburary 2015, Inflammation, vol. 38, pp. 260-271 (Year: 2015).*
Getting, Published Jul. 2006, Pharmacology & Therapeutics, vol. 111, pp. 1-15 (Year: 2016).*
Abdel-Malek et al., Published Dec. 1, 2014, Archives of Biochemistry and Biophysics, vol. 563, pp. 4-12 (Year: 2014).*
English translation of International Preliminary Report on Patentability and Written Opinion mailed Jul. 8, 2021, in PCT/JP2019/051570.
English translation of International Search Report mailed Mar. 10, 2020, in PCT/JP2019/051570.

* cited by examiner

*Primary Examiner* — Yih-Horng Shiao
*Assistant Examiner* — Jaret J Crews
(74) *Attorney, Agent, or Firm* — Birch, Stewart, Kolasch & Birch, LLP

(57) ABSTRACT

The present invention provides a crystal of 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylic acid having a certain quality that can be used as a drug substance. Specifically, the present invention provides a crystal comprising an equimolar amount of 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylic acid and phosphoric acid.

12 Claims, 6 Drawing Sheets

| Size (μm) | Volume In % |
|---|---|
| 0.010 | 0.00 |
| 0.011 | 0.00 |
| 0.013 | 0.00 |
| 0.015 | 0.00 |
| 0.017 | 0.00 |
| 0.020 | 0.00 |
| 0.023 | 0.00 |
| 0.026 | 0.00 |
| 0.030 | 0.00 |
| 0.035 | 0.00 |
| 0.040 | 0.00 |
| 0.046 | 0.00 |
| 0.052 | 0.00 |
| 0.060 | 0.00 |
| 0.069 | 0.00 |
| 0.079 | 0.00 |
| 0.091 | 0.00 |
| 0.105 | |

| Size (μm) | Volume In % |
|---|---|
| 0.105 | 0.00 |
| 0.120 | 0.00 |
| 0.138 | 0.00 |
| 0.158 | 0.00 |
| 0.182 | 0.00 |
| 0.209 | 0.00 |
| 0.240 | 0.00 |
| 0.275 | 0.00 |
| 0.316 | 0.01 |
| 0.363 | 0.10 |
| 0.417 | 0.39 |
| 0.479 | 0.68 |
| 0.550 | 0.95 |
| 0.631 | 1.17 |
| 0.724 | 1.34 |
| 0.832 | 1.45 |
| 0.955 | 1.53 |
| 1.096 | |

| Size (μm) | Volume In % |
|---|---|
| 1.096 | 1.60 |
| 1.259 | 1.71 |
| 1.445 | 1.89 |
| 1.660 | 2.17 |
| 1.905 | 2.59 |
| 2.188 | 3.14 |
| 2.512 | 3.80 |
| 2.884 | 4.55 |
| 3.311 | 5.29 |
| 3.802 | 5.93 |
| 4.365 | 6.37 |
| 5.012 | 6.53 |
| 5.754 | 6.36 |
| 6.607 | 5.89 |
| 7.586 | 5.16 |
| 8.710 | 4.32 |
| 10.000 | 3.45 |
| 11.482 | |

| Size (μm) | Volume In % |
|---|---|
| 11.482 | 2.70 |
| 13.183 | 2.12 |
| 15.136 | 1.75 |
| 17.378 | 1.58 |
| 19.953 | 1.57 |
| 22.909 | 1.66 |
| 26.303 | 1.77 |
| 30.200 | 1.83 |
| 34.674 | 1.81 |
| 39.811 | 1.66 |
| 45.709 | 1.40 |
| 52.481 | 1.03 |
| 60.256 | 0.63 |
| 69.183 | 0.12 |
| 79.433 | 0.01 |
| 91.201 | 0.00 |
| 104.713 | 0.00 |
| 120.226 | |

| Size (μm) | Volume In % |
|---|---|
| 120.226 | 0.00 |
| 138.038 | 0.00 |
| 158.489 | 0.00 |
| 181.970 | 0.00 |
| 208.930 | 0.00 |
| 239.883 | 0.00 |
| 275.423 | 0.00 |
| 316.228 | 0.00 |
| 363.078 | 0.00 |
| 416.869 | 0.00 |
| 478.630 | 0.00 |
| 549.541 | 0.00 |
| 630.957 | 0.00 |
| 724.436 | 0.00 |
| 831.764 | 0.00 |
| 954.993 | 0.00 |
| 1096.478 | 0.00 |
| 1258.925 | |

| Size (μm) | Volume In % |
|---|---|
| 1258.925 | 0.00 |
| 1445.440 | 0.00 |
| 1659.587 | 0.00 |
| 1905.461 | 0.00 |
| 2187.762 | 0.00 |
| 2511.886 | 0.00 |
| 2884.032 | 0.00 |
| 3311.311 | 0.00 |
| 3801.894 | 0.00 |
| 4365.158 | 0.00 |
| 5011.872 | 0.00 |
| 5754.399 | 0.00 |
| 6606.934 | 0.00 |
| 7585.776 | 0.00 |
| 8709.636 | 0.00 |
| 10000.000 | | d(0.1): 1.800 μm   d(0.5): 12.140 μm   d(0.9): 73.991 μm

| Size (μm) | Volume In % |
|---|---|
| 0.010 | 0.00 |
| 0.011 | 0.00 |
| 0.013 | 0.00 |
| 0.015 | 0.00 |
| 0.017 | 0.00 |
| 0.020 | 0.00 |
| 0.023 | 0.00 |
| 0.026 | 0.00 |
| 0.030 | 0.00 |
| 0.035 | 0.00 |
| 0.040 | 0.00 |
| 0.046 | 0.00 |
| 0.052 | 0.00 |
| 0.060 | 0.00 |
| 0.069 | 0.00 |
| 0.079 | 0.00 |
| 0.091 | 0.00 |
| 0.105 | 0.00 |

| Size (μm) | Volume In % |
|---|---|
| 0.105 | 0.00 |
| 0.120 | 0.00 |
| 0.138 | 0.00 |
| 0.158 | 0.00 |
| 0.182 | 0.00 |
| 0.209 | 0.00 |
| 0.240 | 0.00 |
| 0.275 | 0.00 |
| 0.316 | 0.00 |
| 0.363 | 0.01 |
| 0.417 | 0.16 |
| 0.479 | 0.43 |
| 0.550 | 0.69 |
| 0.631 | 0.89 |
| 0.724 | 1.05 |
| 0.832 | 1.13 |
| 0.955 | 1.15 |
| 1.096 | 1.11 |

| Size (μm) | Volume In % |
|---|---|
| 1.096 | 1.04 |
| 1.259 | 0.95 |
| 1.445 | 0.88 |
| 1.660 | 0.83 |
| 1.905 | 0.83 |
| 2.188 | 0.87 |
| 2.512 | 0.97 |
| 2.884 | 1.15 |
| 3.311 | 1.41 |
| 3.802 | 1.78 |
| 4.365 | 2.28 |
| 5.012 | 2.92 |
| 5.754 | 3.69 |
| 6.607 | 4.49 |
| 7.586 | 5.24 |
| 8.710 | 5.76 |
| 10.000 | 5.93 |
| 11.482 | |

| Size (μm) | Volume In % |
|---|---|
| 11.482 | 5.66 |
| 13.183 | 4.93 |
| 15.136 | 3.87 |
| 17.378 | 2.68 |
| 19.953 | 1.65 |
| 22.909 | 0.96 |
| 26.303 | 0.73 |
| 30.200 | 0.99 |
| 34.674 | 1.72 |
| 39.811 | 2.82 |
| 45.709 | 3.99 |
| 52.481 | 4.86 |
| 60.256 | 5.12 |
| 69.183 | 4.69 |
| 79.433 | 3.70 |
| 91.201 | 2.45 |
| 104.713 | 1.27 |
| 120.226 | |

| Size (μm) | Volume In % |
|---|---|
| 120.226 | 0.26 |
| 138.038 | 0.00 |
| 158.489 | 0.00 |
| 181.970 | 0.00 |
| 208.930 | 0.00 |
| 239.883 | 0.00 |
| 275.423 | 0.00 |
| 316.228 | 0.00 |
| 363.078 | 0.00 |
| 416.869 | 0.00 |
| 478.630 | 0.00 |
| 549.541 | 0.00 |
| 630.957 | 0.00 |
| 724.436 | 0.00 |
| 831.764 | 0.00 |
| 954.993 | 0.00 |
| 1096.478 | 0.00 |
| 1258.925 | |

| Size (μm) | Volume In % |
|---|---|
| 1258.925 | 0.00 |
| 1445.440 | 0.00 |
| 1659.587 | 0.00 |
| 1905.461 | 0.00 |
| 2187.762 | 0.00 |
| 2511.886 | 0.00 |
| 2884.032 | 0.00 |
| 3311.311 | 0.00 |
| 3801.894 | 0.00 |
| 4365.158 | 0.00 |
| 5011.872 | 0.00 |
| 5754.399 | 0.00 |
| 6606.934 | 0.00 |
| 7585.776 | 0.00 |
| 8709.636 | 0.00 |
| 10000.000 | 0.00 |

CRYSTAL OF PYRROLIDINE COMPOUND

TECHNICAL FIELD

The present invention relates to a crystal comprising 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylic acid (hereinafter also referred to as "Pyrrolidine compound A" or "Compound A") and phosphoric acid. More specifically, the present invention relates to a crystal comprising an equimolar amount of the Pyrrolidine compound A and phosphoric acid having excellent properties as a drug substance (hereinafter also referred to as "Present crystal"), a pharmaceutical composition comprising the same as an active ingredient, and the like.

BACKGROUND ART

WO 2015/182723 pamphlet (hereinafter also referred to as Patent Document 1) discloses pyrrolidine compounds or pharmacologically acceptable salts thereof having melanocortin 1 receptor (MC1R) agonistic activities (agonist activities), also discloses that these compounds and pharmaceutical compositions comprising these compounds as active ingredients are useful for the treatment or prevention of various diseases of which pathological conditions are expected to be improved by the activation of MC1R, and discloses hydrochloride of the Pyrrolidine compound A in Example 19. However, the Patent Document 1 does not disclose or suggest a crystal of the Pyrrolidine compound A.

CITATION LIST

Patent Document

Patent Document 1: WO 2015/182723 pamphlet

SUMMARY OF THE INVENTION

Problems to be Solved by the Invention

An object of the present invention is to provide a crystal of the Pyrrolidine compound A having a certain quality that can be used as a drug substance.

Means to Solve Problems

It has been found that hydrochloride of the Pyrrolidine compound A is not crystallized, has deliquescency, and thus is not suitable as a drug substance of a pharmaceutical. Thus, the present inventors have tried to crystallize the Pyrrolidine compound A under more than 1000 conditions in order to obtain a crystal having a certain quality that can be used as a drug substance. As a result, the present inventors have found that a crystal comprising an equimolar amount of the Pyrrolidine compound A and phosphoric acid is a crystal having a certain quality that can be used as a drug substance in terms of purity, thermal stability, hygroscopicity, deliquescency, chemical stability, and safety, and finally completed the present invention.

Further, it has also been found that said crystal comprising an equimolar amount of the Pyrrolidine compound A and phosphoric acid has a difficulty in crystallization. Thus, the present inventors have studied the conditions for reproducibly obtaining a crystal having sufficient purity within a short time. The present inventors have found problems such as increase in impurities, delay in precipitation, and deterioration of stirring fluidity and filterability due to micrinization of crystal, depending on crystallization temperature and crystallization solvent composition. In order to solve these problems, the present inventors have earnestly studied the type, amount, ratio, and the like of reagents and solvents to be used in the crystallization as well as crystallization procedure and the like, and finally found a method for effectively producing a crystal having suitable properties as a drug substance such as reduced impurities and excellent handling ease in filtration and the like.

The present invention relates to the followings.

[1]
A crystal comprising an equimolar amount of 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylic acid and phosphoric acid.

[2]
The crystal according to [1] consisting of an equimolar amount of 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylic acid and phosphoric acid.

[3]
The crystal according to any of [1] or [2] which is a cocrystal of 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylic acid and phosphoric acid.

[4]
The crystal according to any one of [1] to [3] which shows peaks at 5.7°, 11.5°, 13.9°, 19.0°, and 21.9° (±0.2° for each peak) as diffraction angles expressed in 2θ in a powder X-ray diffraction spectrum.

[5]
The crystal according to any one of [1] to [4] which has an endothermic peak at 230° C. to 240° C. in a differential scanning calorimetry analysis.

[6]
The crystal according to any one of [1] to [5] which is produced by adding a seed crystal to a mixture of 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylic acid, phosphoric acid, and a good-solvent.

[7]
The crystal according to any one of [1] to [6] which is produced by adding an anti-solvent to a mixture of 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylic acid, phosphoric acid, and a good-solvent; adding a seed crystal thereto; and then further adding an anti-solvent thereto.

[8]
A melanocortin 1 receptor agonist comprising the crystal according to any one of [1] to [7] as an active ingredient.

[9]
A pharmaceutical composition comprising the crystal according to any one of [1] to [7] and a pharmaceutically acceptable additive.

[10]
The pharmaceutical composition according to [9] for preventing or treating a disease of which a pathological condition is expected to be improved by the activation of melanocortin 1 receptor.

[11]

The pharmaceutical composition according to [10], wherein the disease is one or more disease(s) selected from rheumatoid arthritis, gouty arthritis, osteoarthrosis, inflammatory bowel disease, systemic sclerosis, psoriasis, fibrosis, protoporphyria, systemic lupus erythematosus, melanoma, skin cancer, vitiligo, hair loss, pain, ischemia/reperfusion damage, cerebral inflammatory disease, hepatitis, septicemia/septic shock, nephritis, transplantation, HIV disease exacerbation, vasculitis, uveitis, retinitis pigmentosa, age-related macular degeneration, microbial infection, celiac disease, nephrotic syndrome, and melanoma invasion.

[12]

A method for preventing or treating a disease of which a pathological condition is expected to be improved by the activation of melanocortin 1 receptor, the method comprising administering an effective amount of the crystal according to any one of [1] to [7] to a patient.

[13]

Use of the crystal according to any one of [1] to [7] in the manufacture of a medicament for preventing or treating a disease of which a pathological condition is expected to be improved by the activation of melanocortin 1 receptor.

[14]

The crystal according to any one of [1] to [7] for preventing or treating a disease of which a pathological condition is expected to be improved by the activation of melanocortin 1 receptor.

The present invention also relates to the followings.

[15]

A method for producing the crystal according to any one of [1] to [5], which comprises adding a seed crystal to a mixture of 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylic acid, phosphoric acid, and a good-solvent.

[16]

The method according to [15], which comprises adding an anti-solvent to a mixture of 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylic acid, phosphoric acid, and a good-solvent; adding a seed crystal thereto; and then further adding an anti-solvent thereto.

Effect of Invention

A crystal comprising an equimolar amount of the Pyrrolidine compound A and phosphoric acid is a crystal in which solvent(s) used in obtaining the crystal does/do not remain, which is excellent in thermal stability, stable under humid conditions with reduced weight change, not deliquescent, excellent in chemical stability, and does not comprise a compound that may cause adverse effects on living bodies in terms of safety. Said crystal can be reproducibly produced by an industrially suitable method, and thus is useful as a drug substance.

BRIEF DESCRIPTION OF DRAWINGS

FIG. 5-1 is a figure showing a particle size distribution of crystals produced in the Condition 1 of the Experimental Example 7.

FIG. 5-2 is a figure showing a particle size distribution of crystals produced in the Condition 3 of the Experimental Example 7.

MODE FOR CARRYING OUT THE INVENTION

Figure 1:
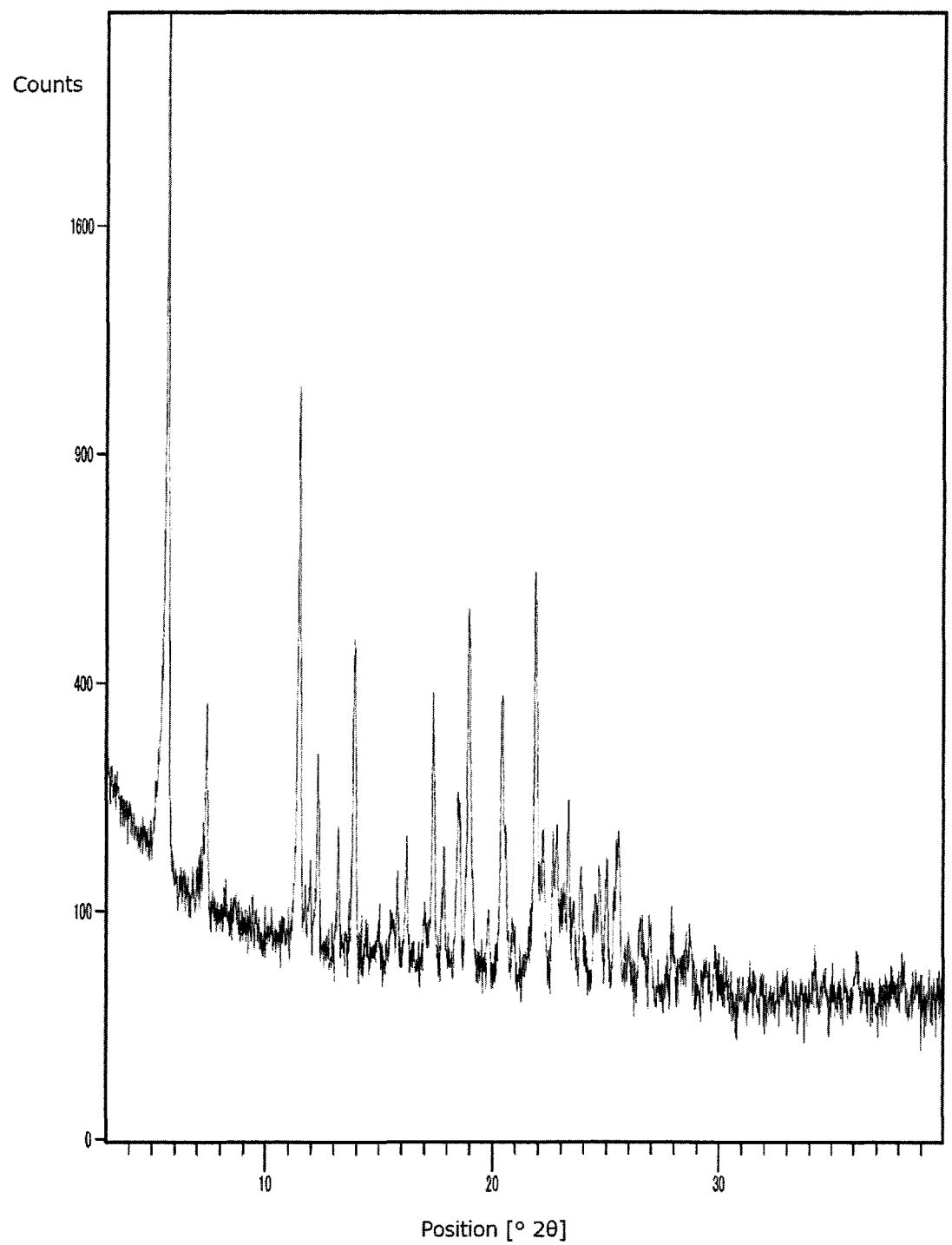
FIG. 1 is a figure showing a result of a powder X-ray diffraction measurement of a Present crystal.

The present invention relates to a crystal comprising an equimolar amount of the Pyrrolidine compound A and phosphoric acid represented by the following formula, a pharmaceutical composition comprising the same as an active ingredient, and the like.

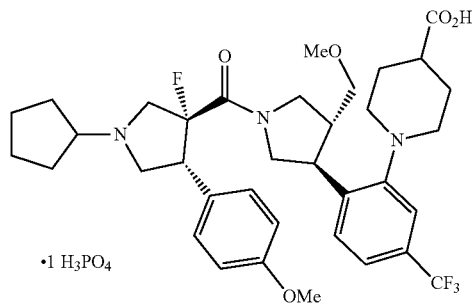 [SMILES: COC[C@H]1CN(C(=O)[C@]2(F)CN(C3CCCC3)C[C@H]2c2ccc(OC)cc2)C[C@@H]1c1ccc(C(F)(F)F)cc1N1CCC(C(=O)O)CC1]

The Pyrrolidine compound A and/or phosphoric acid in the Present crystal encompass(es) compounds labeled with isotopes (for example, $^{3}H$, $^{13}C$, $^{14}C$, $^{15}N$, $^{18}F$, and $^{32}P$) or the like, and deuterated products.

In the present invention, the crystal comprising an equimolar amount of the Pyrrolidine compound A and phosphoric acid is a crystal in which other molecules such as solvent(s) used in obtaining the crystal do not remain, and thus is a crystal which comprises the Pyrrolidine compound A and phosphoric acid at a molar ratio of 1:1, i.e., comprises 1 molar equivalent of phosphoric acid relative to the Pyrrolidine compound A.

Preferable aspects of the Present crystal include a cocrystal wherein the Pyrrolidine compound A and phosphoric acid do not form a salt, and the Pyrrolidine compound A and phosphoric acid are bound with each other at a molar ratio of 1:1 by a non-ionic bond and/or a non-covalent bond. In one aspect, the Present crystal shows a powder X-ray diffraction pattern in FIG. 1, and the characteristic peaks thereof include peaks at 5.7°, 11.5°, 13.9°, 19.0°, and/or 21.9° (±0.2° for each peak) as diffraction angles expressed in 2θ, more specific peaks thereof include peaks at 5.7°, 11.5°, 13.9°, 17.4°, 19.0°, 20.4°, and/or 21.9° (±0.2° for each peak) as diffraction angles expressed in 2θ, further more specific peaks thereof include peaks at 5.70, 7.40, 11.50, 12.30, 13.90, 17.40, 19.00, 20.4°, and/or 21.9° (±0.2° for each peak) as diffraction angles expressed in 2θ, and especially specific peaks thereof include peaks listed in Table 2 described below as diffraction angles expressed in 2θ (hereinafter a crystal having these peaks is also referred to as "Form B crystal" or "Phosphoric acid Form B crystal"). In another aspect, the above Form B crystal shows a differential scanning calorimetry (hereinafter also referred to as "DSC") curve in FIG. 2, and has an endothermic peak at 230° C. to 240° C.

The Present crystal has an advantageous effect in that the amount of residual solvent(s) is below the standard value determined by the International Council for Harmonisation of Technical Requirements for Pharmaceuticals for Human Use (hereinafter referred to as "ICH"). Also, other effects of the Present crystal include that the amounts of organic impurities, inorganic impurities, residual metals, residual solvents, genotoxic impurities, and the like are below the standard values determined in the guideline of ICH.

Further, the Present crystal is preferably prepared as a crystal having 7 μm or more, more preferably 7 to 15 μm, and especially preferably 8 to 12 μm of mode diameter of non-cohesive crystal. The "mode diameter" is the particle size in which the volume % of the particle size distribution becomes the maximum value. In the method for producing the Present crystal, when at least 70% or more, preferably 80% or more, and more preferably 90% or more crystals among the whole crystals have said mode diameter, handling ease such as ease in filtering the crystals is improved.

The Present crystal may be prepared by, for example, reacting 1 mol of the Pyrrolidine compound A, which may be prepared according to the method of Example 19 in the Patent Document 1, with 1 to 10 mol, and preferably 1 to 5 mol of phosphoric acid. Besides this, the Present crystal may also be prepared according to the methods described below in the Examples.

Solvents to be used for obtaining the Present crystal may be appropriately selected, and, for example, good-solvents or anti-solvents may be used alone or in their appropriate combinations. The good-solvents are not limited as long as they can highly dissolve the Pyrrolidine compound A, and examples thereof include ketones (for example, acetone and 2-butanone), esters (for example, ethyl acetate and methyl acetate), alcohol (for example, methanol, ethanol, and i-propanol), and mixtures of these solvents. The anti-solvents are not limited as long as they poorly dissolve the Pyrrolidine compound A, and examples thereof include water, alkanes (for example, hexane and heptane), aromatic hydrocarbons (for example, benzene and toluene), ethers (for example, diethyl ether, dimethyl ether, and diisopropyl ether), and mixtures of these solvents.

One aspect of the method for producing the Present crystal is a method wherein to a mixture of the Pyrrolidine compound A and a good-solvent is added phosphoric acid, to the resulting mixture is added a seed crystal, and the resulting crystals are filtered. A preferable aspect is a method wherein the Pyrrolidine compound A is dissolved into a good-solvent, phosphoric acid is added thereto, to the resulting mixture is added a seed crystal, and then the resulting crystals are filtered. A more preferable aspect is a method wherein the Pyrrolidine compound A is dissolved into ethyl acetate or ethanol, phosphoric acid is added thereto, to the resulting mixture is added a seed crystal, and then the resulting crystals are filtered.

Also, another aspect is a method wherein to a mixture of the Pyrrolidine compound A and a good-solvent is added phosphoric acid, to the resulting mixture is added an anti-solvent, and the resulting crystals are filtered. A preferable aspect is a method wherein the Pyrrolidine compound A is dissolved into a good-solvent, phosphoric acid is added thereto, to the resulting mixture is added an anti-solvent, then a seed crystal is added thereto, and the resulting crystals are filtered. A more preferable aspect is a method wherein the Pyrrolidine compound A is dissolved into a good-solvent, phosphoric acid is added thereto, to the resulting mixture is added an anti-solvent, then a seed crystal is added thereto, an anti-solvent is further added thereto, and the resulting crystals are filtered. A further more preferable aspect is a method wherein the Pyrrolidine compound A is dissolved into a good-solvent, phosphoric acid is added thereto, to the resulting mixture is added water, then a seed crystal is added thereto, water is further added thereto, and the resulting crystals are filtered.

When a good-solvent and an anti-solvent are used in combination, examples of preferable combination and ratio include ethanol:toluene=1:9, ethanol:diisopropyl ether=3:7, and acetone toluene=3:7. When a good-solvent is used in combination with water, examples of preferable good-solvent include ethyl acetate and ethanol. When a good-solvent is used in combination with an anti-solvent, specifically water, and water is added twice before and after the addition of a seed crystal, the amount of water added before the addition of a seed crystal (first addition of water) is preferably 3 times by volume ratio relative to the weight of the Pyrrolidine compound A, and the amount of water added after the addition of a seed crystal (second addition of water) is preferably 4.5 times by volume ratio relative to the weight of the Pyrrolidine compound A. Another aspect is a method wherein the amount of water added is 5 to 10 times by volume ratio relative to the weight of the Pyrrolidine compound A, and water is added dividedly before and after the addition of a seed crystal. More preferably, the amount of water is 6 to 9 times, and still more preferably 7.5 times by volume ratio relative to the weight of the Pyrrolidine compound A. In another aspect, the volume ratio of the amount of the first addition of water to the amount of the second addition of water is 1:1 to 1:2, and preferably 2:3. In another aspect, water is added before the addition of a seed crystal so that 70% or more, and preferably 80% or more crystals precipitate after the addition of a seed crystal and before the addition of water. Also, examples of temperature in the addition of a seed crystal include 28 to 32° C., and preferably 30° C. These temperatures are also preferably selected so that 70% or more, and preferably 80% or more crystals precipitate after the addition of a seed crystal and before the addition of water.

A seed crystal of the Present crystal may be prepared by the method described below in Example 3, Experimental Example 2, or Experimental Example 3. Also, the resulting crystal prepared by these methods may be used as a seed crystal of the Present crystal, and subjected to, for example, the method described in Example 1 or 2 or a method according to the method described in Example 1 or 2 to prepare a seed crystal.

Because the Present crystal has human MC1R agonist activities, it can be used as an active ingredient of a melanocortin 1 receptor agonist, and the Present crystal and a pharmaceutical composition comprising the same as an active ingredient are useful for the treatment or prevention of various diseases of which pathological conditions are expected to be improved by the activation of MC1R. Examples of such diseases include one or more disease(s) selected from rheumatoid arthritis, gouty arthritis, osteoarthrosis, inflammatory bowel disease, systemic sclerosis, psoriasis, fibrosis, protoporphyria (for example, erythropoietic protoporphyria), systemic lupus erythematosus, melanoma, skin cancer, vitiligo, hair loss, pain, ischemia/reperfusion damage, cerebral inflammatory disease, hepatitis, septicemia/septic shock, nephritis, transplantation, HIV disease exacerbation, vasculitis, uveitis, retinitis pigmentosa, age-related macular degeneration, microbial infection, celiac disease, nephrotic syndrome, and melanoma invasion Especially, the Present crystal is useful for the treatment or prevention of one or more disease(s) and the like selected from systemic sclerosis, psoriasis, protoporphyria, melanoma, skin cancer, vitiligo, hair loss, retinitis pigmentosa, age-related macular degeneration, and nephrotic syndrome. In particular, the Present crystal is useful for the treatment or prevention of one or more disease(s) and the like selected from systemic sclerosis, protoporphyria, melanoma, vitiligo, retinitis pigmentosa, age-related macular degeneration, and nephrotic syndrome.

The pharmaceutical composition comprising the Present crystal as an active ingredient may be prepared by mixing the Present crystal and pharmaceutically acceptable additive(s) such as excipient(s), disintegrator(s), binder(s), lubricant(s), coating agent(s), colorant(s), diluent(s), base(s), and isotonic agent(s).

The Present crystal and the pharmaceutical composition comprising the same as an active ingredient may be prepared into an appropriate dosage form such as powder, injection, tablet, capsule, and topical preparation, and then administered to a patient by using an appropriate method of administration in accordance with the dosage form such as intravenous administration, oral administration, and percutaneous administration. The term "patient" used in the present invention is an individual to be prevented or treated by the Present crystal, preferably a mammal, and more preferably a human.

The dose may be determined depending on the patient's age, body weight, general health condition, sex, diet, time of administration, method of administration, excretion rate, a combination of drugs, and the severity of the disease state of the patient under treatment at the time of administration, in consideration of these or other factors. The Present crystal and the pharmaceutical composition comprising the same as an active ingredient have low toxicity and can be safely used. The daily dose (i.e., effective amount) thereof may vary depending on the condition or body weight of the patient, the administration route, or the like. For example, in the case of parenteral administration, the Present crystal is desirably administered at a dose of approximately 0.0001 to 1000 mg/person/day, preferably approximately 0.001 to 1000 mg/person/day, and especially preferably 0.01 to 500 mg/person/day, and in the case of oral administration, the Present crystal is desirably administered at a dose of approximately 0.0001 to 1000 mg/person/day, and preferably 0.01 to 500 mg/person/day.

In the present invention, the term "prevention (or prevent)" means an action to administer the Present crystal or the pharmaceutical composition comprising the same to an individual who has not developed an illness, a disease, or a symptom. Also, the term "treatment (or treat)" means an action to administer the Present crystal or the pharmaceutical composition comprising the same to an individual who has already developed an illness, a disease, or a symptom. Accordingly, an action to administer the Present crystal or the pharmaceutical composition comprising the same to an individual who have already developed an illness, a disease, or a symptom in order to prevent the deterioration, attack, or relapse of the symptom and the like is one aspect of "treatment (or treat)".

EXAMPLES

Hereinafter, the present invention is illustrated more in detail by Examples and Experimental Examples, but the present invention is not limited by them. In EXAMPLES, "equivalent" means "molar equivalent".

Example 1: Synthesis of the Present Crystal

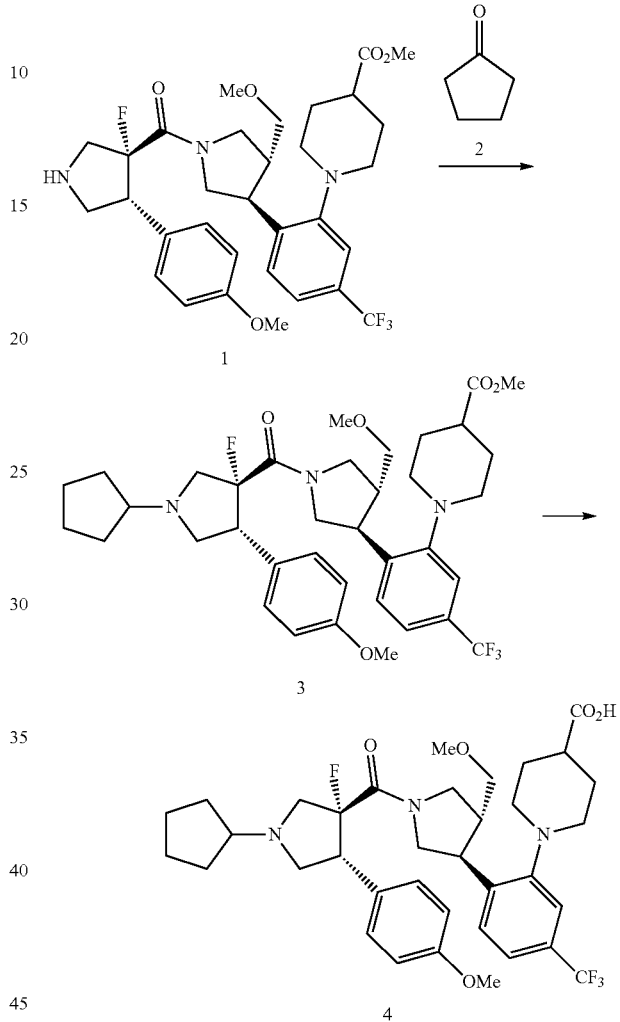

The Compound 1 (26.18 g) was dissolved into dichloromethane (207 mL), the Compound 2 (4.4 mL) and acetic acid (3.56 mL) were added thereto, and the resulting mixture was stirred under room temperature for 30 minutes. Then, sodium triacetoxyborohydride (13.2 g) was added thereto, and the resulting mixture was stirred under room temperature for 1 hour. An aqueous solution of saturated sodium hydrogen carbonate was added thereto, the resulting mixture was stirred, and then extracted with dichloromethane. The resulting organic layer was washed with saturated brine, dried over magnesium sulfate, and concentrated under reduced pressure. The resulting residue was purified by NH silica gel column chromatography (hexane:ethyl acetate=75: 25 to 55:45), and then silica gel column chromatography (chloroform:methanol=100:0 to 95:5) to give the Compound 3 (24.25 g) as colorless powder (MS (ESI): m/z 690 [M+H]$^+$).

The Compound 3 (24.24 g) was dissolved into methanol (240 mL), an aqueous solution of sodium hydroxide (2 mol/L, 70.2 mL) was added thereto, and the resulting mixture was stirred under room temperature for 19 hours. Then, hydrochloric acid (2 mol/L, 74 mL) was added thereto, and then the resulting reaction solution was concentrated under reduced pressure. To the concentrated residue were added water and ethyl acetate, the resulting mixture was stirred, and then extracted with ethyl acetate. The resulting organic layer was washed with a phosphate buffer solution (0.1 mol/L, 300 mL) and brine, dried over magnesium sulfate, and concentrated under reduced pressure. The resulting residue was purified by silica gel column chromatography (chloroform:methanol=100:0 to 90:10), then dissolved into ethyl acetate, a phosphate buffer solution (0.1 mol/L, 200 mL) was added thereto, the resulting mixture was stirred under room temperature, and extracted with ethyl acetate. The resulting organic layer was washed with water and saturated brine, dried over magnesium sulfate, and concentrated under reduced pressure to give the Compound 4 (23.7 g) as colorless powder (MS (ESI): m/z 676 [M+H]$^+$).

The Compound 4 (135 mg) was dissolved into ethanol (0.7 mL), and a small amount of the Present crystal was added thereto as a seed crystal. To the resulting mixture was added a phosphoric acid solution prepared by dissolving phosphoric acid (25 mg) into ethanol (0.5 mL), ethanol (0.2 mL) was further added thereto, and the resulting mixture was stirred under room temperature overnight. The precipitated crystals were collected by filtration, washed with ethyl acetate (0.6 mL), and then dried under reduced pressure at 50° C. for 4 hours to give the Present crystals (112.7 mg). As a result of confirming the presence or absence of residual solvents by 1H-NMR, no residual solvent was found. A result of elemental analysis measurement is shown in the following Table 1.

TABLE 1

<Result of elemental analysis measurement>

|  | C | H | N | P |
|---|---|---|---|---|
| Measured value | 55.21 | 6.14 | 5.31 | 3.96 |
| Theoretical value | 55.49 | 6.29 | 5.39 | 3.97 |

(The above theoretical value is a theoretical value with 0.3 equivalent of attached water.)

<Powder X-Ray Diffraction (Hereinafter Also Referred to as XRPD) Measurement>

XRPD was measured by using a powder X-ray diffraction measurement device X'PertPro (manufactured by PANalytical B.V.) under the following conditions.
  X-ray generator: X-ray tube (Anticathode: copper, Tube voltage: 45 kV, Tube current: 40 mA)
  Incidence optical system: Focusing condensing mirror
    Light-receiving optical system: High-speed semiconductor array detector (X-Celerator), Extended light-receiving side arm
  Sample stage: HTS sample stage (oscillated at the range of 4 mm in the X-axis direction)
  Cumulated number: 5 times (each incidence angle was changed by −2, −1, 0, 1, and 2°, respectively)
  Measurement range: 2θ=3 to 40°
  Scan speed: 0.668451°/sec
  Step: 0.0167°

The results are shown in FIG. 1. When the peak intensity at 5.7° as a diffraction angle expressed in 2θ is set to be 100, peaks having 5 or more as the relative peak intensity are as shown in the following Table 2.

TABLE 2

| 2θ (°) | Relative intensity (%) |
|---|---|
| 5.7 | 100.0 |
| 7.4 | 13.4 |
| 11.5 | 47.4 |
| 12.3 | 10.8 |
| 13.2 | 6.5 |
| 13.9 | 23.0 |
| 16.2 | 5.7 |
| 17.4 | 17.1 |
| 17.9 | 5.7 |
| 18.5 | 9.2 |
| 19.0 | 30.3 |
| 20.4 | 17.2 |
| 21.9 | 39.9 |
| 22.2 | 5.6 |
| 22.8 | 7.2 |
| 23.3 | 7.3 |
| 23.9 | 6.0 |
| 24.7 | 5.9 |
| 25.0 | 6.9 |
| 25.5 | 7.2 |

<Differential Scanning Calorimetry (DSC) Measurement>

Figure 2:
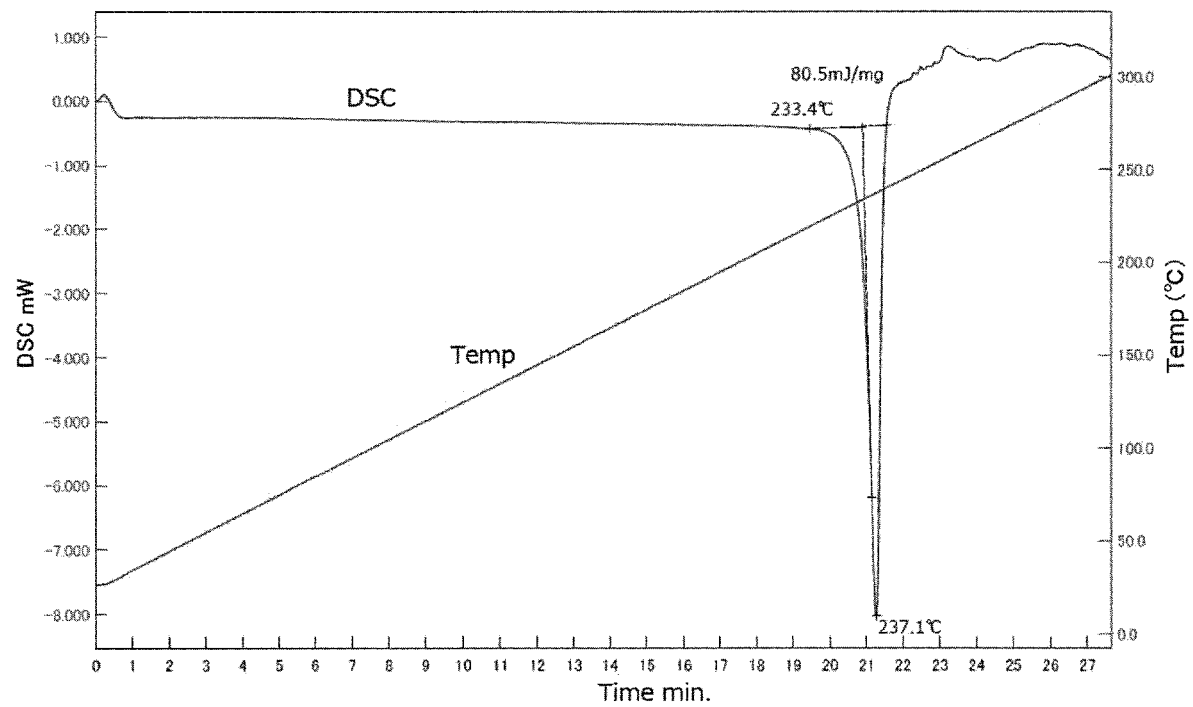
FIG. 2 is a figure showing a result of differential scanning calorimetry of a Present crystal.

DSC was measured by using a differential scanning calorimetry device X-DSC7000 (SII NanoTechnology Inc.) under the following conditions.
  Rate of temperature increase: 10° C./min (25° C. to 300° C.)
  Atmosphere: nitrogen 100 mL/min The results are shown in FIG. 2. An endothermic peak at about 230° C. to 240° C. was observed.

<Single Crystal X-Ray Diffraction Measurement>

To ethanol (2 mL) was added the Present crystals having about half volume of a spatula (small size) to be dissolved thereto, the resulting solution was left to stand at room temperature for 4 days, and crystallized. The structure of the resulting crystal was analyzed with a single crystal X-ray diffraction device R-AXIS RAPID/R (Rigaku Corporation) (CuKα radiation) by determining lattice constants at 23° C., measuring diffraction peak intensities, then determining the phases by direct method, and carrying out a structure refinement by full matrix least square method. The resulting crystallographic data and crystal structure analysis results are shown in Table 3. The reliability factor (R factor) was 3.06%, and the other several parameters also demonstrated that the present crystal structure analysis was a sufficiently highly reliable analysis result.

TABLE 3

Crystallographic data and crystal structure analysis results

| Molecular formula | $C_{36}H_{48}F_4N_3O_9P_1$ |
|---|---|
| Molecular weight | 773.76 |
| Lattice constant | a = 8.15 (2) Å |
|  | b = 20.47 (6) Å |
|  | c = 23.87 (7) Å |
|  | α = 90° |
|  | β = 90° |
|  | γ = 90° |
|  | V = 3984 (18) Å$^3$ |
| Crystal system | Orthorhombic system |
| Space group | $P2_12_12_1$ |
| Z value | 4 |
| Number of unique reflections | 6806 |
| Density $D_{calc}$ | 1.290 g/cm$^3$ |
| R factor | 3.06% (I > 2.0 sigma) |
| Flack parameter | 0.02 (3) |

Figure 3:
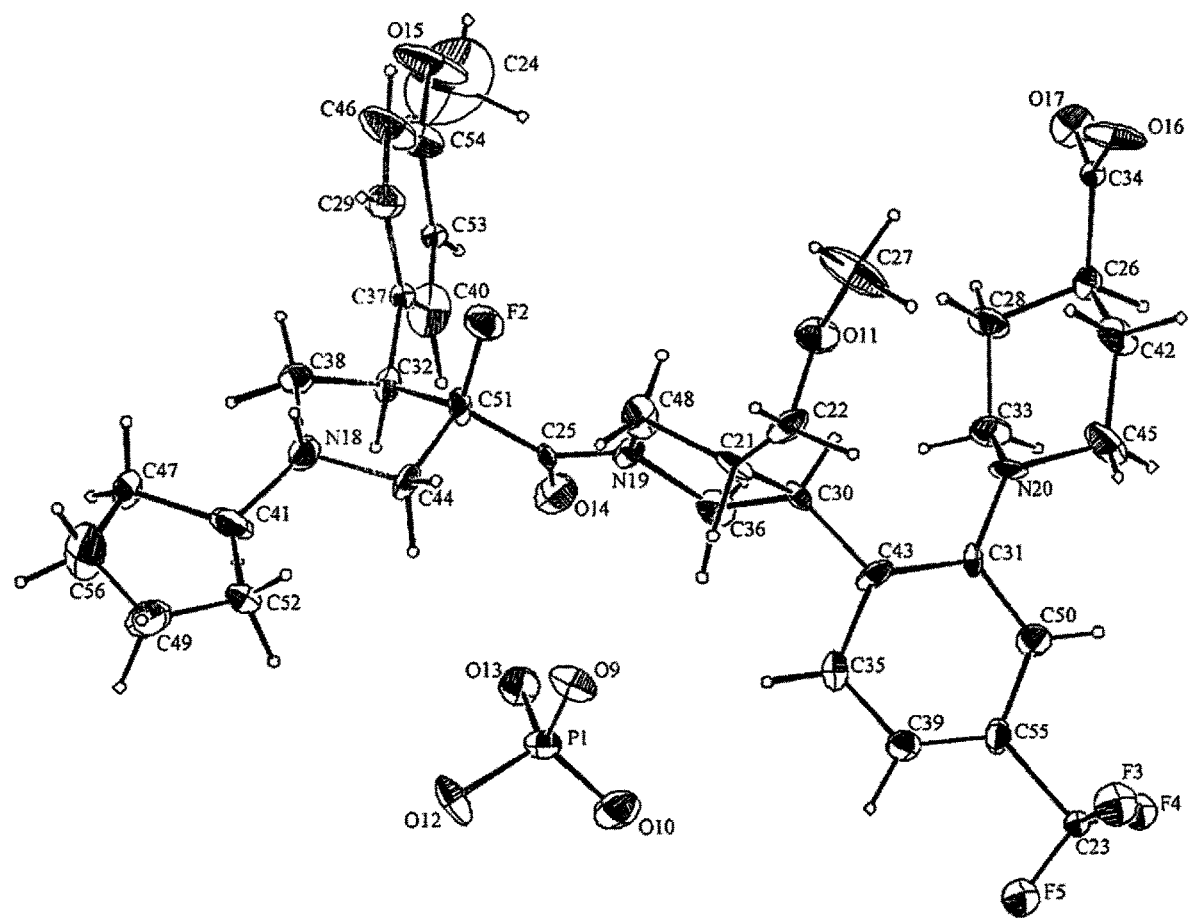
FIG. 3 is a figure showing an ORTEP diagram based on a single crystal X-ray diffraction measurement of molecules in a Present crystal.
Figure 4:
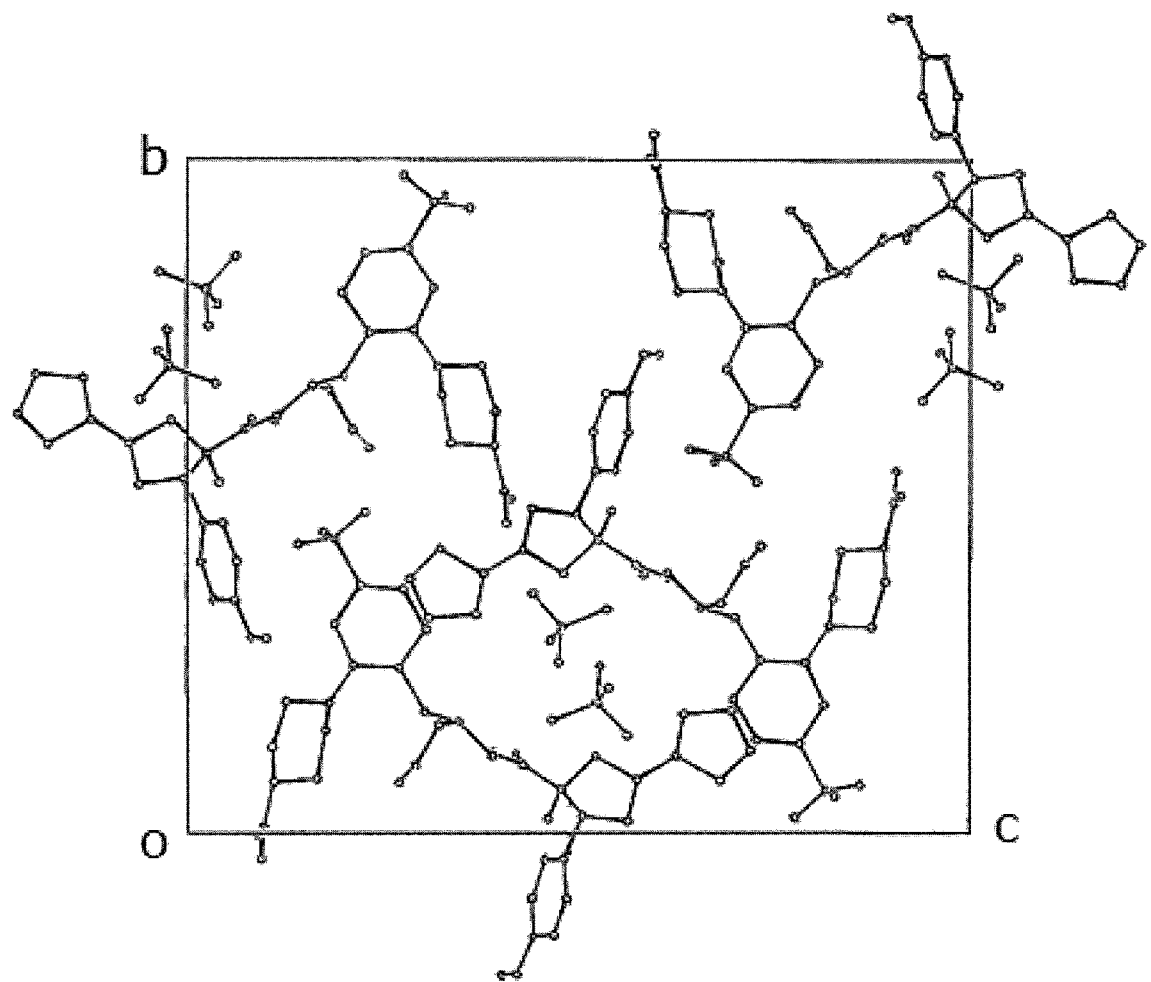
FIG. 4 is a figure showing a packing diagram (a-axis projection) based on a single crystal X-ray diffraction measurement of molecules in a Present crystal.

The ORTEP diagram of molecules in the Present crystal is shown in FIG. 3, and the packing diagram of the Present crystal is shown in FIG. 4. In the crystal, each one molecule of the Pyrrolidine compound A and phosphoric acid was independently present in the asymmetric unit.

As a result of studying the absolute configuration of the Present crystal, the Flack parameter was 0.02 (3), and thus the Present crystal was confirmed to be a crystal having a building block of one molecule of 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylic acid and one molecule of phosphoric acid as shown in FIG. 3.

A guidance (Regulatory Classification of Pharmaceutical Co-Crystals Guidance for Industry) issued by the Food and Drug Administration (FDA) discloses that a cocrystal is a crystal which comprises two or more different kinds of molecules in the crystal lattice that are bound by a non-ionic bond and/or a non-covalent bond. Because the above crystal structure analysis has already confirmed that there is no covalent bond between the Pyrrolidine compound A and phosphoric acid, the presence or absence of an ionic interaction between the Pyrrolidine compound A and phosphoric acid has been studied.

Phosphoric acid is a Bronsted acid. Thus, when an ionic interaction is observed between phosphoric acid and the Pyrrolidine compound A, the Pyrrolidine compound A needs to accept a proton as a Bronsted base. Regarding the Pyrrolidine compound A, three nitrogens (N18, N19, and N20) are able to accept a proton from phosphoric acid. Here, all hydrogen bond sites in the Present crystal are shown in Table 4.

TABLE 4

Hydrogen bond sites in the Present crystal

| Donor | H | Acceptor | Length D...A | Angle D-H...A | Symmetry Operators |
|---|---|---|---|---|---|
| F2 | — | N19 | 2.77 (1) Å | — | — |
| O9 | — | O13 | 2.41 (1) Å | — | X + 1/2 − 1, −Y + 1/2 + 2, −Z + 1 |
| O10 | — | O17 | 2.40 (1) Å | — | −X + 3, Y + 1/2, −Z + 1/2 |
| O12 | — | O14 | 2.56 (2) Å | — | X + 1/2 − 1, −Y + 1/2 + 2, −Z + 1 |
| O13 | — | O9 | 2.41 (1) Å | — | X + 1/2, −Y + 1/2 + 2, −Z + 1 |
| O14 | — | O12 | 2.56 (2) A | — | X + 1/2, −Y + 1/2 + 2, −Z + 1 |
| O16 | — | N18 | 2.70 (2) Å | — | −X + 1/2 + 2, −Y + 2, Z + 1/2 − 1 |
| O17 | — | O10 | 2.40 (1) Å | — | −X + 3, Y + 1/2 − 1, −Z + 1/2 |
| N18 | H18 | O16 | 2.70 (2) Å | 157.9 (8) ° | −X + 1/2 + 2, −Y + 2, Z + 1/2 |

(1) N18

N18 is a nitrogen having a sp3 hybrid orbital, has a highest basicity in the Pyrrolidine compound A, and possibility to accept a proton from phosphoric acid. However, N18 (more strictly, the hydrogen atom bound to N18) forms a hydrogen bond with the oxygen (O16) of the carboxylic acid of the adjacent Pyrrolidine compound A (symmetry operators: −X+1/2+2, −Y+2, Z+1/2), and is deemed to already accept a proton. Thus, N18 cannot accept a proton from phosphoric acid. In addition, all atomic distances to oxygens of phosphoric acids adjacent to N18 exceed the sum of van der Waals' radii, and thus we deem that there is no phosphoric acid within a distance which enables N18 to make an ionic interaction.

(2) N19

N19 is a nitrogen having a sp2 hybrid orbital, thus has a weak basicity, and we deem that it cannot form a salt. In addition, the atomic distance to oxygen (O13) in phosphoric acid in the closest distance to N19 is the sum of van der Waals' radius, and thus we deem that said oxygen is not in a distance capable of an ionic interaction.

(3) N20

N20 is also a nitrogen having a sp2 hybrid orbital, thus has a weak basicity, and we deem that it cannot form a salt. In addition, all atomic distances to oxygens of phosphoric acids adjacent to N20 exceed the sum of van der Waals' radii, and thus we deem that there is no phosphoric acid within a distance which enables N20 to make an ionic interaction.

In view of the above results, it has been proved that the bonds between nitrogens (N18, N19, and N20) in the Pyrrolidine compound A and phosphoric acid in the Present crystal are not caused by an ionic interaction. Thus, we deem that the Pyrrolidine compound A and phosphoric acid do not form a salt, and the Present crystal is a cocrystal. The crystal prepared in the present Examples is referred to as Form B crystal in the present description.

Example 2: Synthesis (2) of the Present Crystal

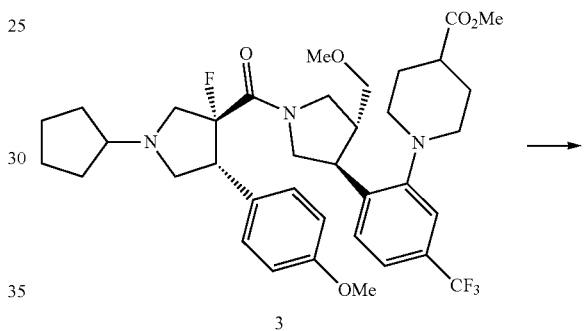

3

-continued

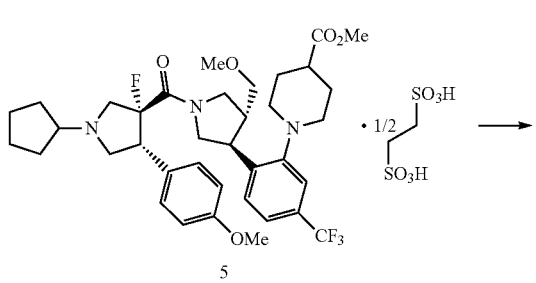

5

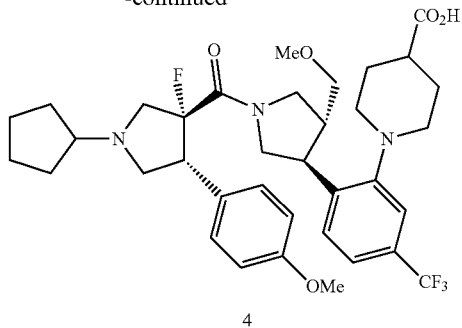

4

To a solution of the Compound 3 (276 mg) in ethanol (1.4 mL) was added 1,2-ethanedisulfonic acid hydrate (38 mg), and the resulting mixture was stirred at room temperature for 40 minutes. The resulting crystals were collected by filtration, and washed twice with ethanol (0.84 mL). The crystals were dried at 40° C. or less to give the Compound 5 (178 mg). To a suspension of the Compound 5 (37.1 kg) in ethyl acetate (167.5 kg) were sequentially added a solution of potassium carbonate (6.5 kg) in water (148.3 L) and water (36.8 L) at room temperature, and the resulting mixture was stirred at room temperature for 15 minutes. The resulting aqueous layer was removed, the resulting organic layer was washed with water (186 L) twice, ethyl acetate (67.2 kg) was added thereto, and undissolved residue was filtered. The resulting filtrate was concentrated to 78 L, then ethanol (146.5 kg) was added thereto, and the resulting mixture was concentrated to 78 L. Ethanol (146.9 kg) was added thereto, and the resulting mixture was concentrated to 56 L. The resulting mixture was diluted with ethanol (44 kg), a 24% aqueous solution of sodium hydroxide (8.7 kg) and water (30.1 kg) were sequentially added thereto at room temperature, and the resulting mixture was stirred at 40° C. for 5 hours to give the Compound 4. To a solution of the Compound 4 were sequentially added a solution of phosphoric acid (12.0 kg) in water (55.7 L) and water (55.7 L) at 30° C. A Present crystal was added thereto as a seed crystal (928 g), and the resulting mixture was stirred for 14 hours. Water (167.0 L) was added thereto, the resulting mixture was stirred for 4 hours, and then cooled to 25° C. The resulting solids were collected by filtration, and said solids were washed with water (182 L). The solids were dried at 50° C. or less to give the Present crystals (35.2 kg). Said crystals were excellent in handling ease such as filterability.

Experimental Example 1: Crystallization Study of the Pyrrolidine Compound A

The Pyrrolidine compound A was subjected to crystallization studies by long storage using 25 kinds of single solvents and 44 kinds of mixed solvents, crystallization studies by 1-month stirring using 96 kinds of mixed solvents prepared from various mixture ratios of 2 kinds of anti-solvents and 12 kinds of good-solvents, and crystallization studies by grinding using 26 kinds of added solvents. As a result, crystals were obtained in the crystallization studies by the long storage and 1-month stirring. As a result of measuring the powder X-ray diffraction of the resulting crystals, the peaks were the same among all crystals, and thus all crystals had the same crystal form. The crystallization conditions were studied, but solvents remained in crystals in all conditions under which crystals were produced. Also, the step for drying crystals was studied, but residual solvents could not become below the standard values of residual solvents established by ICH.

Accordingly, the free form of the Pyrrolidine compound A was crystallized, but solvents used in obtaining the crystals remained and chemical stability thereof was poor. Thus, the free form cannot be used as a drug substance.

Experimental Example 2: Crystallization Study (1) of Mixture Comprising the Pyrrolidine Compound A The Pyrrolidine compound A (about 900 mg) was dissolved into tetrahydrofuran (30 mL), and each 100 μL thereof was dispensed in each vial of a 96 well plate (about 3 mg/vial). Also, 21 kinds of acids such as phosphoric acid, hydrochloric acid, L(−)-malic acid, L(+)-tartaric acid, maleic acid, sulfuric acid, and malonic acid and 8 kinds of bases such as sodium hydroxide and L-arginine (hereinafter also referred to as counter compounds) were dissolved into 8 kinds of solvents described below to prepare each 0.1 mol/L solution (0.05 mol/L solution for several acids), and each 45 μL (90 μL for said several acids) thereof was dispensed in each vial. Solvents were allowed to evaporate by opening the plate for one day-and-night, and then the plate was dried under reduced pressure for 4 hours. Each 250 μL of 8 kinds of solvents such as ethyl acetate, acetone, and toluene was dispensed in each vial, then each vial was stirred by ultrasonic wave for 5 minutes, sealed, and stirred at room temperature for 6 days. Regarding the vials having precipitates, the precipitates were collected by filtration, and each XRPD thereof was measured. Regarding the vials having no precipitate, solvents were allowed to evaporate at room temperature, and if solids were observed, the solids were collected by filtration and each XRPD thereof was measured. The XRPD measurement device and measurement conditions were the same as Example 1.

The vials of a combination of phosphoric acid and ethyl acetate, a combination of L(−)-malic acid and toluene, a combination of L(+)-tartaric acid and acetone, and a combination of maleic acid and toluene precipitated Phosphoric acid Form A crystals, L(−)-Malic acid Form D crystals, L(+)-Tartaric acid Form E crystals, and Maleic acid Form F crystals, respectively. Other than these vials, there were vials in which crystals of counter compounds only, i.e., crystals free of the Pyrrolidine compound A were observed. Meanwhile, the vials to which hydrochloric acid was added did not precipitate a crystal for all 8 kinds of solvents. Further, the vials to which sulfuric acid, malonic acid, or L-arginine was added also did not precipitate a crystal for all solvents.

Experimental Example 3: Crystallization Study (2) of Mixture Comprising the Pyrrolidine Compound A The Pyrrolidine compound A (about 800 mg) was dissolved into tetrahydrofuran (40 mL), and each 100 μL thereof was dispensed in each vial of a 96 well plate (about 2 mg/vial). Also, 22 kinds of acids such as phosphoric acid, hydrochloric acid, L(−)-malic acid, L(+)-tartaric acid, maleic acid, sulfuric acid, and malonic acid, and 8 kinds of bases such as sodium hydroxide and L-arginine (hereinafter also referred to as counter compounds) were dissolved into 12 kinds of solvents described below to prepare each 0.1 mol/L solution (0.05 mol/L solution for several acids), and each 30 μL (60 μL for said several acids) thereof was dispensed in each vial. After the dispensing, nitrogen was sprayed thereto, and solvents were allowed to evaporate. Each 200 μL of 12 kinds of solvents such as mixed solvents of ethanol and toluene with mixture ratios of 3:7 and 1:9, a mixed solvent of ethanol and diisopropyl ether with a mixture ratio 3:7, mixed solvents of acetone and toluene with mixture ratios of 3:7 and 1:9, and a mixed solvent of ethyl acetate and heptane with a mixture ratio of 3:7 was dispensed in each vial, each vial was sealed, and stirred at room temperature for 3 days. Regarding the vials having precipitates, the precipitates were collected by filtration, and each XRPD thereof was measured. Regarding the vials having no precipitate, solvents were allowed to evaporate at room temperature, and if solids were observed after about 1 month, the solids were collected and each XRPD thereof was measured. The XRPD measurement device and measurement conditions were the same as Example 1.

The combinations in vials which precipitated crystals are shown in the following Table 5. In the Table, the symbol "-" means that a crystal was not produced, and the symbols such as "A" and "B" mean that a Form A crystal and a Form B crystal etc. were produced, respectively. Namely, the Maleic acid Form F crystal obtained in the present Experimental Example had the same XRPD pattern as the Maleic acid Form F crystal obtained in the Experimental Example 2, and the Phosphoric acid Form B crystal obtained in the present Experimental Example was different from the Phosphoric acid Form A crystal obtained in the Experimental Example 2. Also, other than these crystals, there were vials in which crystals of counter compounds only were observed like the Experimental Example 2. Meanwhile, the vials to which hydrochloric acid was added did not precipitate a crystal for all 12 kinds of solvents. Further, L(-)-malic acid and L(+)-tartaric acid precipitated crystals in the Experimental Example 2, but did not precipitate a crystal in the present Experimental Example for all 12 kinds of solvents.

0.1 mol/L solution, and each 30 μL thereof was dispensed in each vial. After the dispensing, nitrogen was sprayed thereto to allow the solvents to evaporate, then 200 μL of toluene was dispensed in the vial to which L(-)-malic acid was added, 200 μL of acetone was dispensed in the vial to which L(+)-tartaric acid was added, and 200 μL of a mixed solvent of ethyl acetate and heptane with a mixture ratio of 3:7 was dispensed in the vial to which sulfuric acid was added, then sealed to prepare each sample, and eight vials were prepared for each sample. The total of 24 vials were stirred at room temperature for 7 days, but all vials did not result in a precipitate.

<L-Arginine>

The Pyrrolidine compound A (about 65 mg) was dissolved into ethanol (0.3 mL) and toluene (2.1 mL) at room temperature to prepare a solution. L-Arginine (about 19 mg) was dissolved into ethanol (0.6 mL) and water (0.6 mL), and added to the above solution of the Pyrrolidine compound A. Because the mixture was a solution, nitrogen was sprayed thereto to allow the solvents to evaporate, and then a syrup partially comprising white powder was produced. Said syrup was dissolved into ethanol (0.3 mL) again, and diisopropyl ether (0.6 mL) was added dropwise thereto. The L-Arginine Form K crystal obtained in the Experimental Example 3 was added thereto as a seed crystal, but dissolved thereto. Thus, toluene (1.2 mL) was added thereto, and the resulting mixture was stirred for one day-and-night. Because the mixture was a solution, nitrogen was sprayed thereto to allow the solvents to evaporate. The resulting residue was subjected to a XRPD measurement to confirm that it was amorphous. Heptane (0.6 mL) was added thereto, the resulting mixture was stirred at room temperature overnight, and then observed by a microscope. As a result, a crystal ingredient was not observed.

TABLE 5

Results of crystallization study (2) of mixture comprising the Pyrrolidine compound A

| | Phosphoric acid | Maleic acid | Malonic acid | Sulfuric acid | L-Arginine |
|---|---|---|---|---|---|
| Ethanol:Toluene = 3:7 | — | F | H | — | — |
| Ethanol:Toluene = 1:9 | B | F | H | — | K |
| Ethanol:Diisopropyl ether = 3:7 | B | — | — | — | — |
| Acetone:Toluene = 3:7 | B | F | H | — | — |
| Acetone:Toluene = 1:9 | — | F | G | — | — |
| Ethyl acetate:Heptane = 3:7 | — | — | H | J | — |

Experimental Example 4: Crystallization Study (3) of Mixture Comprising the Pyrrolidine Compound A Among the crystals obtained in the Experimental Examples 2 and 3, reproducibility was confirmed for crystals other than the Phosphoric acid Form A crystal and Phosphoric acid Form B crystal. As a result, the L(-)-Malic acid Form D crystal, L(+)-Tartaric acid Form E crystal, Sulfuric acid Form J crystal, and L-Arginine Form K crystal could not be obtained again. Meanwhile, the combination of maleic acid and malonic acid precipitated crystals again.

<L(-)-Malic Acid, L(+)-Tartaric Acid, and Sulfuric Acid>

The Pyrrolidine compound A (about 80 mg) was dissolved into tetrahydrofuran (4 mL), and each 100 μL thereof was dispensed in each vial of a 96 well plate (about 2 mg/vial). Also, L(-)-malic acid, L(+)-tartaric acid, and sulfuric acid were dissolved into solvents described below to prepare a <Maleic Acid Form F Crystal>

The Pyrrolidine compound A (about 65 mg) was dissolved into toluene (0.5 mL) at room temperature. Thereto were added a solution of maleic acid (about 13 mg) in ethanol (75 μL) and a small amount of a previously obtained Maleic acid Form F crystal as a seed crystal. The resulting reaction solution was gel-like (agar-like) and could not be stirred. Toluene (1.0 mL) was additionally added thereto, and the resulting mixture was vigorously rubbed with a spatula to give a suspension. The resulting crystals were collected by filtration, and dried under reduced pressure at 40° C. for 5 hours to give the Maleic acid Form F crystals (57 mg). 1H-NMR confirmed that 0.1 equivalent of toluene remained in the resulting crystals.

<Malonic Acid Form G Crystal>

The Pyrrolidine compound A (about 325 mg) was dissolved into acetone (1 mL) at room temperature. Malonic acid (55 mg) was dissolved into acetone (0.5 mL) at room temperature, and the resulting solution was added to the above solution of the Pyrrolidine compound A. To said solution was added dropwise toluene (6 mL). A small amount of the Malonic acid Form I crystal described below was added thereto as a seed crystal, and the resulting mixture was stirred at room temperature for two nights. The total amount of the mixture was filtered, and dried under reduced pressure at 40° C. for 3.5 hours to give crystals (317 mg). 1H-NMR confirmed that the resulting crystals contained 1 equivalent of toluene. In order to replace toluene with water, said crystals were stored under the conditions of 25° C. and 70% RH for 72 hours by using a Dynamic Vapour Sorption (DVS) device. As a result, amorphization of said crystals was observed.

<Malonic Acid Form H Crystal>

The Pyrrolidine compound A (about 65 mg) was dissolved into a mixed solvent (2 mL) of ethyl acetate and heptane with a mixture ratio of 3:7 at room temperature. Malonic acid (11 mg) was dissolved into ethyl acetate (0.3 mL) at room temperature, and the resulting solution was added to the above solution of the Pyrrolidine compound A. To the resulting hard gummy syrup was added ethyl acetate (3 mL) to give a suspension. The resulting mixture was stirred at room temperature for 3 days, then solvents were allowed to evaporate by spraying nitrogen, to the resulting dried solids was added ethyl acetate (3 mL), the resulting mixture was stirred, and heptane (1.2 mL) was gradually added thereto. To the resulting mixture was added a small amount of the Malonic acid Form G crystal obtained in the Experimental Example 3 as a seed crystal to rapidly give precipitates. The mixture was stirred at room temperature for two nights, then the total amount thereof was filtered, and dried under reduced pressure at 40° C. for 3.5 hours to give crystals (38 mg).

<Malonic Acid Form I Crystal>

The Pyrrolidine compound A (about 65 mg) was dissolved into a mixed solvent (2.3 mL) of acetone and toluene with a mixture ratio of 1:9 at room temperature. Malonic acid (11 mg) was dissolved into acetone (0.1 mL) at room temperature, and the resulting solution was added to the above solution of the Pyrrolidine compound A. The resulting mixture was stirred at room temperature for three nights, the total amount thereof was filtered, and dried under reduced pressure at 40° C. for 2 hours to give crystals (51 mg). 1H-NMR confirmed that the resulting crystals contained 1 equivalent of toluene. Because said crystals might be toluene adducts, said crystals were further dried under reduced pressure to confirm whether solvent-free crystals could be produced. Said crystals (about 5 mg) were dried under reduced pressure at 60° C. for 4 hours to confirm that toluene (about 0.5 equivalent) remained therein and the crystal form was not changed.

Example 3: Synthesis (3) of the Present Crystal

Each amount of the Pyrrolidine compound A and phosphoric acid shown in the following Table 6 was added to each solvent shown in the following Table 6, and the resulting mixture was stirred for each time shown in the following Table 6. The results are shown in the following Table 6. The XRPD measurement device and measurement conditions were the same as the Example 1. In the XRPD results, "A" means the same crystal as the Phosphoric acid Form A crystal obtained in the Experimental Example 2, and "B" means the same crystal as the Phosphoric acid Form B crystal obtained in the Experimental Example 3. Further, the Phosphoric acid Form B crystal was the same as the Present crystal obtained in the Example 1.

TABLE 6

| | Compound A (mg) | Phosphoric acid (mg) | Solvent | Reaction time | Yield (mg) | XRPD |
|---|---|---|---|---|---|---|
| (a) | 135 | 25 (1.1 equiv.) | Ethyl acetate 6 mL | 1 week | 73 | A + B |
| (b) | 65 | 13 (1.1 equiv.) | Ethyl acetate 3 mL Water 6 μL | 9 days | 38 | B |
| (c) | 135 | 25 (1.1 equiv.) | Ethyl acetate 6 mL | 10 days | 129 | B |
| (d) | 65 | 18 (1.6 equiv.) | Ethanol 0.5 mL Toluene 4.5 mL | 4 days | Not measured due to syrup | |
| (e) | 65 | 18 (1.6 equiv.) | Ethanol 2.1 mL Diisopropyl ether 4.9 mL | 8 days | 36 | B |
| (f) | 65 | 18 (1.6 equiv.) | Acetone 1.5 mL Toluene 3.5 mL | 1 day | 44 | C |

In the method (a), a mixture of Form A crystals and Form B crystals was produced. The elemental analysis results of said crystals proved that they contained 1.5 equivalents of phosphoric acid. In the method (f) using an acetone/toluene solvent, novel Form C crystals were produced. The elemental analysis results of said Form C crystals proved that they contained 2 equivalents of phosphoric acid. Also, all methods could not produce the Form A crystal alone.

In the methods (a), (b), (c), (e), and (f), an amorphous or a syrup was produced just after the addition of phosphoric acid. Said amorphous was stirred at room temperature for 7 to 10 days or said syrup was frequently rubbed with a spatula for a long period of time to give crystals. In the method (d), a suspension of crystals was produced one day after the start of crystallization, but turned into a syrup by stirring at room temperature for 4 days. Further, solvents were evaporated by nitrogen, and the resulting product was stirred in ethanol at room temperature overnight to give the Form B crystals.

Experimental Example 5: Synthesis of Hydrochloride of the Pyrrolidine Compound A

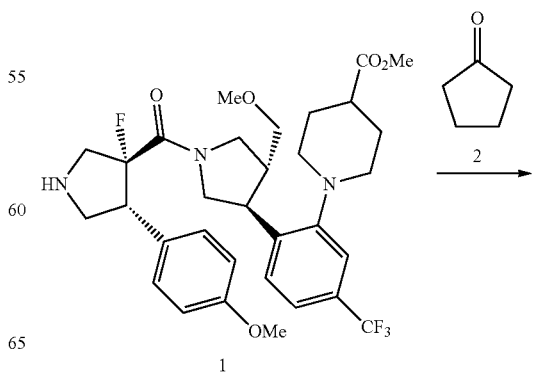

1

-continued

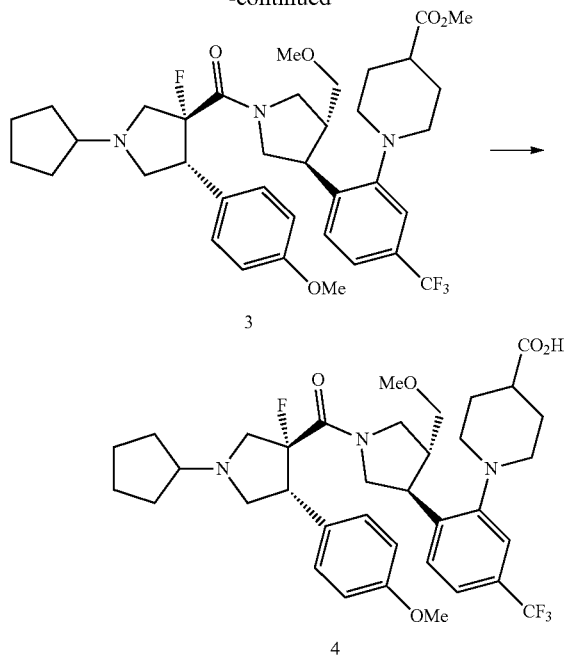

To a solution of the Compound 1 (19.43 g) in chloroform (157 mL) were added the Compound 2 (3.3 mL) and acetic acid (2.7 mL), the resulting mixture was stirred at room temperature for 30 minutes, then sodium triacetoxyborohydride (10.0 g) was added thereto, and the resulting mixture was stirred at room temperature for 20 hours. An aqueous solution of saturated sodium hydrogen carbonate was added thereto, the resulting mixture was stirred, and then extracted with chloroform. The resulting organic layer was washed with an aqueous solution of saturated sodium hydrogen carbonate and saturated brine, dried over magnesium sulfate, and concentrated under reduced pressure. The resulting residue was purified by NH silica gel column chromatography (hexane:ethyl acetate=75:25 to 55:45), then silica gel column chromatography (chloroform:methanol=100:0 to 95:5), and silica gel column chromatography (chloroform:methanol=99:1 to 96:4) to give the Compound 3 (21.92 g) as colorless powder (MS (ESI): m/z 690 [M+H]$^+$).

To a solution of the Compound 3 (21.91 g) in methanol (200 mL) was added an aqueous solution of sodium hydroxide (2 mol/L, 63.6 mL), and the resulting mixture was stirred at room temperature for 3 hours. Hydrochloric acid (2 mol/L, 63.6 mL) was added thereto, and then the resulting reaction mixture was concentrated under reduced pressure. To the concentrated residue were added water and ethyl acetate, the resulting mixture was stirred, and then extracted with ethyl acetate. The resulting organic layer was washed with saturated brine, dried over magnesium sulfate, and concentrated under reduced pressure. The resulting residue was purified by silica gel column chromatography (chloroform:methanol=98:2 to 90:10), then dissolved into ethyl acetate, a phosphate buffer solution (0.1 mol/L, 300 mL) was added thereto, and the resulting mixture was stirred at room temperature for 3 hours. The mixture was extracted with ethyl acetate, then the resulting organic layer was washed with saturated brine, dried over magnesium sulfate, and concentrated under reduced pressure to give the Compound 4 (17.40 g) as colorless powder (MS (ESI): m/z 676 [M+H]$^+$).

To a solution of the Compound 4 (17.40 g) in ethyl acetate (250 mL) was added a solution of hydrochloric acid in ethyl acetate (4 mol/L, 31.8 mL), and the resulting mixture was stirred at room temperature for 30 minutes. The solvent was distilled off under reduced pressure, diethyl ether was added thereto, the resulting mixture was stirred, then filtered, and dried under reduced pressure to give hydrochloride (17.43 g) of the Compound 4 as colorless powder (MS (ESI): m/z 676 [M+H]$^+$).

Experimental Example 6: Comparison of Amorphous of Hydrochloride of the Pyrrolidine Compound A, Amorphous of the Pyrrolidine Compound A, Crystal of the Pyrrolidine Compound A, and Reproducible Crystal of Mixture Comprising the Pyrrolidine Compound A Hydrochloride of the Pyrrolidine compound A described in Example 19 of the Patent Document 1 is amorphous, and the subsequent studies have not resulted in a crystal of hydrochloride of the Pyrrolidine compound A (see the above Experimental Examples 2 and 3). Thus, the amorphous of hydrochloride of the Pyrrolidine compound A was used in the comparative tests. In the following comparative test results, the "hydrochloride" is hydrochloride of the Pyrrolidine compound A which is the compound obtained according to the method described in the Experimental Example 5.

In the following comparative test results, the "amorphous of free form" is the amorphous of free form of the Pyrrolidine compound A which is the Compound 4 obtained according to the method described in the Example 1.

In the following comparative test results, the "crystal of free form" is the crystal of free form of the Pyrrolidine compound A. Regarding said crystal, the residual solvent(s) in the crystal cannot become below the standard values established by ICH as shown in the Experimental Example 1, and it has been already confirmed that said crystal is not a suitable crystal as a drug substance.

In the following comparative test results, the "Phosphoric acid Form A+Form B crystal" is the crystal obtained according to the method (a) described in the Example 3, the "Phosphoric acid Form B crystal" is the Present crystal obtained according to the method described in the Example 1, the "Phosphoric acid Form C crystal" is the crystal obtained according to the method (f) described in the Example 3, and the "Maleic acid Form F crystal" is the Maleic acid Form F crystal obtained according to the method described in the Experimental Example 4.

In the following comparative test results, the "Malonic acid Form H crystal" is the Malonic acid Form H crystal obtained according to the method described in the Experimental Example 4. Other than Malonic acid Form H crystal, Form G and Form I crystals were obtained for malonic acid, but these crystals contain toluene in the molecules. Because toluene is known to be a compound causing damages to central nervous system and the like, it is not preferable to contain toluene in a drug substance in terms of safety and it is clear that the Form G and Form I crystals are not suitable for drug substances. Thus, these crystals were not subjected to a comparative test.

Regarding the above each crystal, thermal stability, hygroscopicity or deliquescency, and chemical stability were evaluated.

<Thermal Stability Evaluation>

Thermal stability was evaluated by using a thermogravimetry/differential thermal analyzer TG/DTA7200 (SII NanoTechnology Inc.) under the following conditions.

Rate of temperature increase: 10 K/min
Atmosphere: nitrogen 200 mL/min

<Hygroscopicity or Deliquescency Evaluation>

Hygroscopicity or deliquescency was evaluated as follows by using a moisture adsorption measurement device DVS-1 or DVS-intrinsic (Surface Measurement Systems Limited). Each sample was placed into a cell of which the tare weight had been corrected in advance, and the cell was hung on the precision balance of said device to precisely measure the weight at the start of measurement. The humidity was changed in a stepwise manner, the weight change was recorded with time, and the equilibrium weight was calculated at each humidity. On the basis of the weight of anhydride converted from the amount of water at a dried condition (0% RH) or at the start of measurement observed by an alternative method, the weight change rate at each humidity was calculated.

<Chemical Stability Evaluation>

Each sample was stored at 60° C. under a sealed condition and at 60° C. under 75% RH for 1 week, an increase or decrease of related substances after the storage was calculated by high-performance liquid chromatographic method on the basis of the area percentage of each peak. Also, the condition of each sample after the storage was observed.

The results are shown in the following Table 7.

TABLE 7

| Sample | Amorphous of hydrochloride | Amorphous of free form | Crystal of free form | Phosphoric acid Form A + Form B crystal |
|---|---|---|---|---|
| Thermal stability TG: weight change | 4.8% 30-150° C. | 2.2% 30-130° C. | | 2.4% 30-130° C. |
| Hygroscopicity or Deliquescency Weight change under 90% RH Chemical stability | 11.87% deliquescent | 1.8% | | 5.2% |
| 60° C., sealed | 0.23% | 0.31% | | −0.05% |
| 60° C., 75% RH | 4.46% deliquescent | 0.30% | | 3.66% |
| Remarks | | | residual solvent(s) could not become below the standard values established by ICH | containing 1.5 equivalents of phosphoric acid |

| Sample | Phosphoric acid Form B crystal | Phosphoric acid Form C crystal | Maleic acid Form F crystal | Malonic acid Form H crystal |
|---|---|---|---|---|
| Thermal stability TG: weight change | No change 30-230° C. | 2.7% 30-70° C. | 3% 30-120° C. | 2% 30-110° C. |

TABLE 7-continued

| | | | | |
|---|---|---|---|---|
| Hygroscopicity or Deliquescency Weight change under 90% RH Chemical stability | <1% | 6.8% | 2.4% | about 6.5% |
| 60° C., sealed | 0.02% | 0.03% | 0.07% | 0% |
| 60° C., 75% RH | 0.05% | 7.13% deliquescent | 1.59% deliquescent | 1.07% deliquescent |
| Remarks | Present crystal containing 1 equivalent of phosphoric acid | containing 2 equivalents of phosphoric acid | 0.1 equivalent of toluene remained | |

As reproducible solids of the Pyrrolidine compound A and mixtures comprising the same, the amorphous of hydrochloride, amorphous of free form, crystal of free form, Phosphoric acid Form A+Form B crystal, Phosphoric acid Form B crystal which is one aspect of the Present crystal, Phosphoric acid Form C crystal, Maleic acid Form F crystal, Malonic acid Form G crystal, Malonic acid Form H crystal, and Malonic acid Form I crystal have been found. Among them, the crystal of free form could not make the residual solvent(s) below the standard values established by ICH, and the Malonic acid Form G crystal and Malonic acid Form I crystal contained toluene in the molecules and were not suitable crystals as drug substances in terms of safety. Similarly, the Maleic acid Form F crystal also could not completely remove the residual solvent, i.e., toluene. Meanwhile, the Present crystal contains no confirmable residual solvent, does not contain toluene in the molecules, and thus is believed to be a problem-free crystal in terms of safety.

Also, the amorphous of hydrochloride, Phosphoric acid Form C crystal, Maleic acid Form F crystal, and Malonic acid Form H crystal were all deliquescent, while the Phosphoric acid Form B crystal was not deliquescent. Further, regarding the Phosphoric acid Form B crystal, the weight change under 90% RH was below 1%, and the increase of related substances was 0.05% only even after the storage at 60° C. under 75% RH for 1 week. Thus, the Phosphoric acid Form B crystal was proved to be stable against humid conditions, and a chemically very stable crystal.

Further, the amorphous of free form and Phosphoric acid Form A+Form B crystal showed 2% or more of weight change by heating to 130° C. Meanwhile, the Phosphoric acid Form B crystal did not show a weight change even at 200° C. or more, and thus was proved to be a crystal having excellent thermal stability.

Experimental Example 7: Study of Precipitation Conditions of the Present Crystal

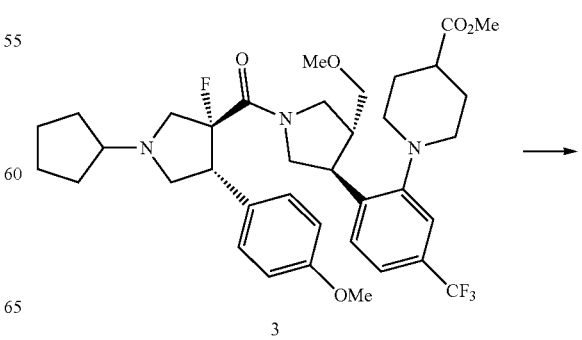

3

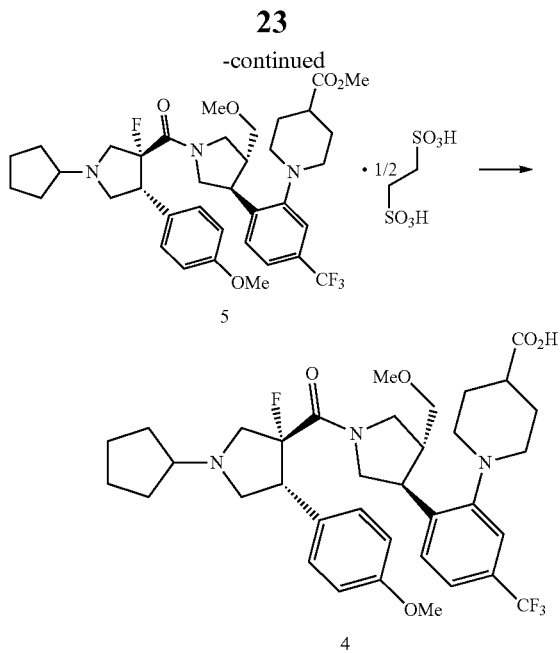

Condition 1

To a solution of the Compound 5 (15.00 g) in ethyl acetate (67.75 g) was added dropwise an aqueous solution of potassium carbonate (2.64 g of potassium carbonate in 75 mL of purified water) at 25° C., and the resulting mixture was stirred at 300 rpm for 30 minutes. The resulting organic layer was separated, washed with purified water, and then concentrated under reduced pressure. Ethanol (59.03 g) was added thereto, and the resulting mixture was concentrated under reduced pressure until the volume became 27 mL, and such procedure was repeated twice.

To the resulting concentrated mixture was added ethanol (24.32 g) until the volume became 45 mL, a 24% aqueous solution of sodium hydroxide (4.79 g) and purified water (12 mL) were added dropwise thereto at 25° C., and the resulting mixture was stirred at 300 rpm for 6 hours. To the reaction mixture were added dropwise a 85% aqueous solution of phosphoric acid (6.61 g) and purified water (22.5 mL, which was 1.5 times amount by volume ratio relative to the weight of the Compound 4) over 5 minutes, and then purified water (90 mL, which was 6.0 times amount by volume ratio relative to the weight of the Compound 4) was added dropwise thereto over 30 minutes. After the addition of purified water, the resulting mixture was stirred for 30 minutes, the reaction temperature was raised to 35° C., and a seed crystal (0.3746 g, which was 0.025 time amount by weight ratio relative to the weight of the Compound 4) was added thereto. After 10 hours following the addition of the seed crystal, the reaction temperature was set to be 20° C., the reaction mixture was stirred for additional 30 minutes, then insoluble matters were collected by filtration, and dried under reduced pressure to give the Present crystals (7.48 g).

The resulting crystals had handling difficulty, because they had poor filterability, required time for filtration, and the wet body thereof before drying was slurry.

Figures 1, 5:
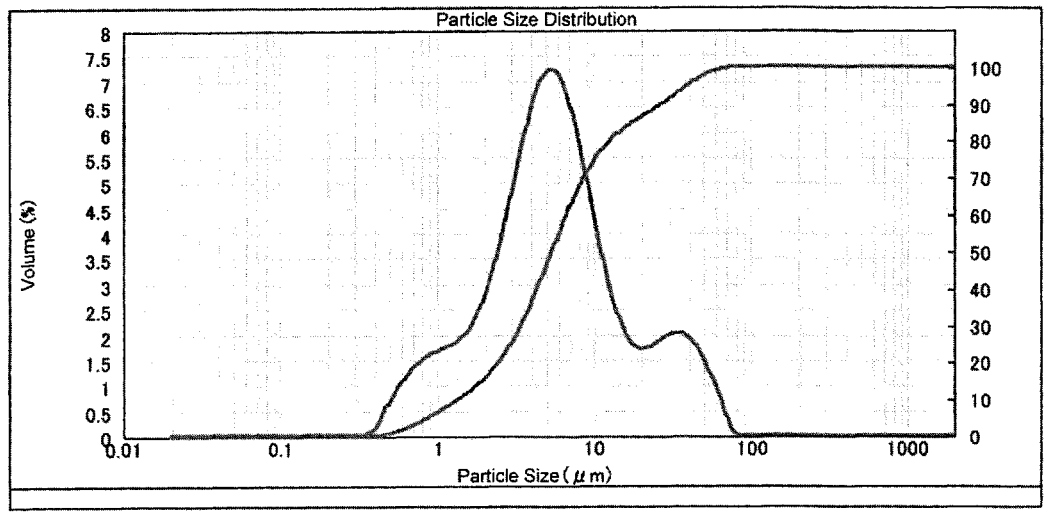
Figures 2, 5:
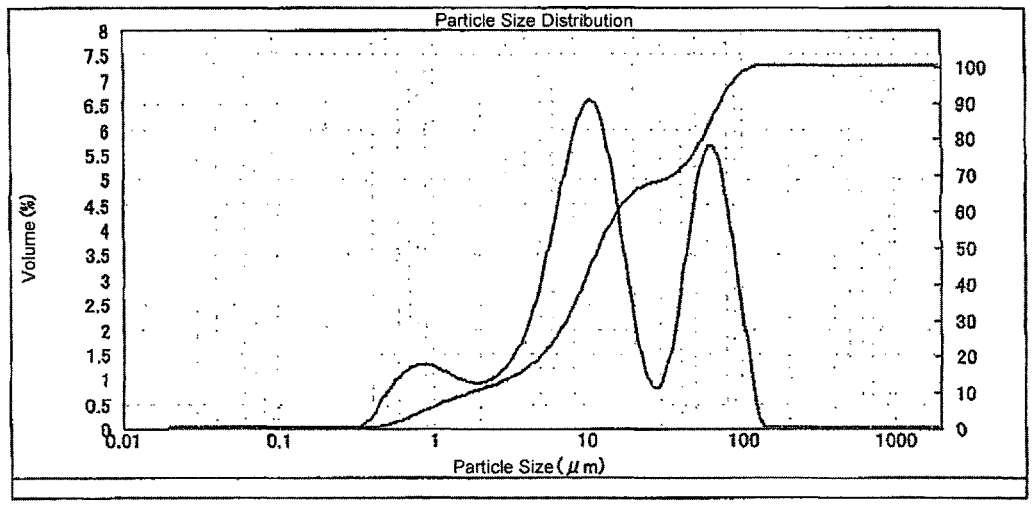

The particle size of the resulting crystals was measured, and the mode diameter thereof was about 6 µm. The particle size distribution of the crystals obtained under the Condition 1 was measured (FIG. 5-1).

Condition 2

To a solution of the Compound 3 (17.58 g) in ethanol (53.20 g) were added an aqueous solution of sodium hydroxide (24%, 4.67 g) and purified water (16.20 g), and the resulting mixture was stirred at 40° C. for 3 hours to give a solution of the Compound 4 (73.14 g). To a part of the resulting solution of the Compound 4 (18.28 g) were added phosphoric acid (1.91 g, 2.6 equivalents) and purified water (7.49 g, which was 1.5 times amount by volume ratio relative to the weight of the Compound 4) at 35° C., the resulting mixture was stirred for 1 hour, and then a seed crystal (125 mg, which was 0.025 time amount by weight ratio relative to the weight of the Compound 4) was added thereto. After 17 hours and 30 minutes following the addition of the seed crystal, purified water (30.0 mL, which was 6.0 times by volume ratio relative to the weight of the Compound 4) was added thereto over 2 hours. After 10 hours, the reaction temperature was set to be 20° C., and the reaction mixture was kept stirring. After 27 hours, the resulting solids were collected by filtration, and said solids were washed with purified water (25.23 g, which was 5 times amount by volume ratio relative to the weight of the Compound 4). The solids were dried at 50° C. to give the Present crystals (4.01 g).

The reaction mixture was sampled after 16 hours and 21 hours following the addition of the seed crystal, quantified by HPLC, and each precipitation rate of the crystals were calculated. As a result, the precipitation rates were 4% and 97%, respectively.

It was found that when the amount of purified water before the addition of a seed crystal was small like the Condition 2, the crystal precipitation rate became extremely low. Namely, it was found that the amount of purified water to be added to the ethanol solution, i.e., the composition of crystallization solvent was important in order to precipitate the Present crystal. Also, when purified water was additionally added to a solution having a low precipitation rate, crystals were precipitated. However, such crystals had handling difficulty in filtration etc. like crystals obtained in the Condition 1.

Condition 3

To a solution of the Compound 3 (26.37 g) in ethanol (79.82 g) were added an aqueous solution of sodium hydroxide (24%, 7.01 g) and purified water (24.30 g), and the resulting mixture was stirred at 40° C. for 4 hours and 30 minutes to give a solution of the Compound 4. To the resulting solution of the Compound 4 were added phosphoric acid (9.70 g, 2.2 equivalents) and purified water (45.00 g, which was 1.5 times amount by volume ratio relative to the weight of the Compound 4) at 20° C., purified water (45.13 g, which was 1.5 times amount by volume ratio relative to the weight of the Compound 4) was further added thereto, the resulting mixture was stirred at 30° C. for 40 minutes, and then a seed crystal (751 mg, which was 0.025 time amount by weight ratio relative to the weight of the Compound 4) was added thereto. After 16 hours, purified water (135 mL, which was 4.5 times by volume ratio relative to the weight of the Compound 4) was added thereto over 2 hours. After 6 hours, the reaction temperature was set to be 20° C., and the reaction mixture was stirred for additional 1 hour. The resulting solids were collected by filtration, and said solids were washed with purified water (150.02 g, which was 5 times amount by volume ratio relative to the weight of the Compound 4). The resulting solids were dried at 50° C. to give the Present crystals (26.95 g). The particle size of the resulting crystals was measured, and the mode diameter thereof was about 10 µm. The resulting crystals had excellent handling ease in filtration and the like. The particle size distribution of crystals obtained under the Condition 3 was measured (FIG. 5-2).

As stated above, the reaction temperature was set to be about 30° C., purified water was added to the reaction mixture at the same amount described in the Condition 3, then a seed crystal was added thereto, the reaction mixture was stirred for a certain period of time to make the resulting crystals grow bigger, and then purified water was further added thereto to give crystals by excellent precipitation rate and handling ease.

TABLE 8

Relationship of amount of purified water added, temperature at which a seed crystal was added, and precipitation rate in experimental conditions 2 and 3

| Condition | 2 | 3 |
|---|---|---|
| Amount of purified water added before the addition of a seed crystal (volume ratio relative to the weight of the Compound 4) | 1.5 | 3.0 |
| Temperature at which a seed crystal was added (° C.) | 35 | 30 |
| Crystal precipitation rate (%) before the 2nd addition of purified water | 4% | 87% |
| 2nd amount of purified water added (volume ratio relative to the weight of the Compound 4) | 6.0 | 4.5 |
| Crystal precipitation rate (%) before filtration | 97% | 98% |

Reaction Device and Stirring Condition
Condition 2
 Reaction device: EasyMax (registered trademark) (Mettler-Toledo International Inc.)
 Stirring condition: 300 rpm
Condition 3
 Reaction device: OptyMax (registered trademark) (Mettler-Toledo International Inc.)
 Stirring condition: 250 rpm
HPLC Measurement Condition
Device Name:
 Column: GL Science, Inertsil ODS-3V (5 μm, 4.6×150 mm)
 Mobile phase A: water/acetonitrile/trifluoroacetic acid=1900:100:1
 Mobile phase B: water/acetonitrile/trifluoroacetic acid=100:1900:1
Particle Trend Measurement Condition
 Device name: Particle Track (registered trademark) MALVERN, Mastersizer 2000 (wet)
 Measurement range: 0.020 to 2000.000 μm
 Measurement time: 10 seconds
 Measurement intensity range: 3.0 to 20.0%
 Stirring rate: about 2000 rpm As stated above, to a reaction mixture was added an adequate amount of purified water, a seed crystal was added thereto, the reaction mixture was stirred for a certain period of time to make the resulting crystals grow bigger, and then purified water was further added thereto to give crystals comprising many long chord-length crystals having excellent fluidity and filterability with adequate precipitation amount as described in the Condition 3. Said crystals improved handling ease in filtration and the like.

Experimental Example 8: Human MC1R Agonist Measurement

The intracellular cAMP concentration was measured by using the Present crystal according to the following method described in the Experimental Example 1 of the Patent Document 1 to calculated $EC_{50}$ value.
(1) Method for Culturing Cells
 Human MC1R agonist activity measurement was carried out by using human melanoma cell line HBL. Culture of HBL: F-10 Nutrient Mixture containing 10% FCS and Penicillin-streptomycin was used in the culture.
(2) cAMP Assay and Data Calculation
 Each compound solution having each concentration was mixed with a cAMP assay buffer (HBSS (Hank's Balanced Salt Solution) containing 10 mM HEPES and 0.1% BSA), and dispensed into a 96 well plate. HBL was suspended in a cAMP assay buffer containing 0.5 mM IBMX so that the concentration became $5 \times 10^4$/mL, dispensed into the above 96 well plate, then mixed, left to stand at 37° C. for 30 minutes, and then the intracellular cAMP concentration was measured by fluorescence method using Envision (ex. 320 nm, em. 590 nm and 665 nm). Ratio value (665 nm measurement value/590 nm measurement value×10000) was calculated from the resulting data, then the quantitative value of cAMP concentration was calculated by using Prism 5.02, induction % value (% of each sample when the average concentration of cAMP of vehicle was 0% and the average concentration of cAMP of αMSH at 10-6 M was 100%) was calculated, and the $EC_{50}$ value was calculated.
 As a result, the Present crystal showed 5.3 nM as the $EC_{50}$ value, and was proved to be a crystal having a potent human MC1R agonist activity.

INDUSTRIAL APPLICABILITY

The Present crystal does not have a residual solvent used in obtaining the crystal, is excellent in thermal stability, stable due to the reduced weight change under humid conditions, not deliquescent, excellent in chemical stability, free from a compound that may cause adverse effects on living bodies in terms of safety, and can be reproducibly produced by a industrially suitable method, and thus is an excellent crystal as a drug substance.

The invention claimed is:
1. A crystal comprising an equimolar amount of 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylic acid and phosphoric acid, wherein the crystal is measured to show peaks at 5.7°, 11.5°, 13.9°, 19.0°, and 21.9° (±0.2° for each peak) as diffraction angles expressed in 2θ in a powder X-ray diffraction spectrum.
2. The crystal according to claim 1, wherein the crystal consists of an equimolar amount of 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylic acid and phosphoric acid.
3. The crystal according to claim 1, wherein the crystal is a cocrystal of 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylic acid and phosphoric acid.
4. The crystal according to claim 1, wherein the crystal has an endothermic peak at 230° C. to 240° C. in a differential scanning calorimetry analysis.
5. The crystal according to claim 1, wherein the crystal is produced by adding a seed crystal to a mixture of 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-

3-yl]-5-(trifluoromethyl)phenyl}piperidine-4-carboxylic acid, phosphoric acid, and a good-solvent.

6. The crystal according to claim 1, wherein the crystal is produced by adding an anti-solvent to a mixture of 1-{2-[(3S,4R)-1-[(3R,4R)-1-cyclopentyl-3-fluoro-4-(4-methoxyphenyl)pyrrolidine-3-carbonyl]-4-(methoxymethyl)pyrrolidin-3-yl]-5-(trifluoromethyl)phenyl}piperidine-4-carboxylic acid, phosphoric acid, and a good-solvent; adding a seed crystal thereto; and then further adding an anti-solvent thereto.

7. A melanocortin 1 receptor agonist comprising the crystal according to claim 1 as an active ingredient.

8. A pharmaceutical composition comprising the crystal according to claim 1 and a pharmaceutically acceptable additive.

9. The pharmaceutical composition according to claim 8, wherein the pharmaceutical composition is for treating a disease in which a pathological condition is expected to be improved by the activation of melanocortin 1 receptor.

10. The pharmaceutical composition according to claim 9, wherein the disease is one or more disease(s) selected from rheumatoid arthritis, gouty arthritis, osteoarthrosis, inflammatory bowel disease, systemic sclerosis, psoriasis, fibrosis, protoporphyria, systemic lupus erythematosus, melanoma, skin cancer, vitiligo, hair loss, pain, ischemia/reperfusion damage, cerebral inflammatory disease, hepatitis, septicemia/septic shock, nephritis, transplantation, HIV disease exacerbation, vasculitis, uveitis, retinitis pigmentosa, age-related macular degeneration, microbial infection, celiac disease, nephrotic syndrome, or melanoma invasion.

11. A method for treating a disease in which a pathological condition is expected to be improved by the activation of melanocortin 1 receptor, the method comprising administering an effective amount of the crystal according to claim 1 to a patient in need thereof.

12. The crystal according to claim 1, wherein the crystal is for treating a disease in which a pathological condition is expected to be improved by the activation of melanocortin 1 receptor.

* * * * *